(12) United States Patent
Aubert et al.

(10) Patent No.: US 11,370,601 B2
(45) Date of Patent: Jun. 28, 2022

(54) AEROSOL DEVICE FOR HAIR SHAPING AND/OR HAIRSTYLE HOLD

(71) Applicant: L'OREAL, Paris (FR)

(72) Inventors: Lionel Aubert, Saint-Ouen (FR); Céférino Rodrigues, Saint-Ouen (FR); Catherine Tetu, Saint-Ouen (FR)

(73) Assignee: L'OREAL, Paris (FR)

( * ) Notice: Subject to any disclaimer, the term of this patent is extended or adjusted under 35 U.S.C. 154(b) by 15 days.

(21) Appl. No.: 16/491,374

(22) PCT Filed: Mar. 9, 2018

(86) PCT No.: PCT/EP2018/055889
§ 371 (c)(1),
(2) Date: Sep. 5, 2019

(87) PCT Pub. No.: WO2018/162707
PCT Pub. Date: Sep. 13, 2018

(65) Prior Publication Data
US 2020/0016045 A1   Jan. 16, 2020

(30) Foreign Application Priority Data
Mar. 9, 2017   (FR) ..................... 1751945

(51) Int. Cl.
*B05B 1/14* (2006.01)
*B65D 83/14* (2006.01)
*A61K 8/02* (2006.01)
*A61K 8/04* (2006.01)
*A61K 8/34* (2006.01)
*A61K 8/19* (2006.01)
*A61K 8/46* (2006.01)
*A61K 8/81* (2006.01)

(52) U.S. Cl.
CPC .......... *B65D 83/752* (2013.01); *A61K 8/0241* (2013.01); *A61K 8/046* (2013.01); *A61K 8/34* (2013.01); *B05B 1/14* (2013.01); *A61K 8/19* (2013.01); *A61K 8/463* (2013.01); *A61K 8/8135* (2013.01); *A61K 2800/31* (2013.01); *A61K 2800/412* (2013.01); *A61K 2800/87* (2013.01)

(58) Field of Classification Search
CPC ........ A61K 8/0241; A61K 8/046; A61K 8/34; A61K 8/19; A61K 8/463; A61K 8/8135; A61K 8/26; A61K 8/8152; A61K 2800/31; A61K 2800/412; A61Q 5/06; B05B 1/14; B65D 83/752; B65D 83/28
See application file for complete search history.

(56) References Cited

U.S. PATENT DOCUMENTS

| | | |
|---|---|---|
| 2,047,398 A | 7/1936 | Voss et al. |
| 2,102,113 A | 12/1937 | Djordjevitch |
| 2,723,248 A | 11/1955 | Wright |
| 3,161,460 A | 12/1964 | Huber |
| 3,504,862 A | 4/1970 | Lowry |
| 3,579,629 A | 5/1971 | Pasero et al. |
| 3,589,978 A | 6/1971 | Kamal et al. |
| 3,628,733 A | 12/1971 | Kahn |
| 3,716,633 A | 2/1973 | Viout et al. |
| 3,767,125 A | 10/1973 | Gehres et al. |
| 3,792,068 A | 2/1974 | Luedders et al. |
| 3,810,977 A | 5/1974 | Levine et al. |
| 3,836,537 A | 9/1974 | Boerwinkle et al. |
| 3,910,862 A | 10/1975 | Barabas et al. |
| 3,925,542 A | 12/1975 | Viout et al. |
| 3,946,749 A | 3/1976 | Papantoniou |
| 3,966,403 A | 6/1976 | Papantoniou et al. |
| 3,966,404 A | 6/1976 | Papantoniou et al. |
| 3,990,459 A | 11/1976 | Papantoniou |
| 4,031,307 A | 6/1977 | DeMartino et al. |
| 4,128,631 A | 12/1978 | Lundmark et al. |
| 4,129,711 A | 12/1978 | Viout et al. |
| 4,131,576 A | 12/1978 | Iovine et al. |
| 4,137,208 A | 1/1979 | Elliott |
| 4,165,367 A | 8/1979 | Chakrabarti |
| 4,223,009 A | 9/1980 | Chakrabarti |
| 4,282,203 A | 8/1981 | Jacquet et al. |
| 4,289,752 A | 9/1981 | Mahieu et al. |

(Continued)

FOREIGN PATENT DOCUMENTS

| | | |
|---|---|---|
| DE | 2330956 A1 | 1/1974 |
| DE | 102005025016 A1 | 12/2005 |

(Continued)

OTHER PUBLICATIONS

Non-Final Office Action for U.S. Appl. No. 14/399,764, dated Dec. 5, 2018 (now abandoned).
Non-Final Office Action for U.S. Appl. No. 15/523,242, dated Dec. 17, 2018 (now U.S. Pat. No. 10,449,140).
Final Office Action for copending U.S. Appl. No. 14/787,983, dated Dec. 27, 2018.
Final Office Action for copending U.S. Appl. No. 15/523,232, dated Jan. 25, 2019.
Non-Final Office Action for U.S. Appl. No. 15/541,738, dated Feb. 5, 2019 (now U.S. Pat. No. 10,532,880).
Non-Final Office Action for copending U.S. Appl. No. 15/541,741, dated Feb. 27, 2019.
International Search Report for counterpart Application No. POT/EP2015/064780, dated Sep. 14, 2015.

(Continued)

*Primary Examiner* — Ali Soroush
(74) *Attorney, Agent, or Firm* — The Marbury Law Group, PLLC

(57) ABSTRACT

The invention relates to an aerosol device comprising: a container containing a cosmetic composition which comprises at least one fixing polymer, and a dispensing head (3) comprising a body (5) and an end part (7) comprising at least two outlet orifices (12) configured to allow spraying of the composition about a longitudinal axis (Y) of the end part (7) in at least two different directions, the dispensing head (3) comprising at least first (15) and second (16) chambers, through which the composition stream successively passes before it exits via the outlet orifices (12).

21 Claims, 7 Drawing Sheets

(56) References Cited

U.S. PATENT DOCUMENTS

Figure 1:
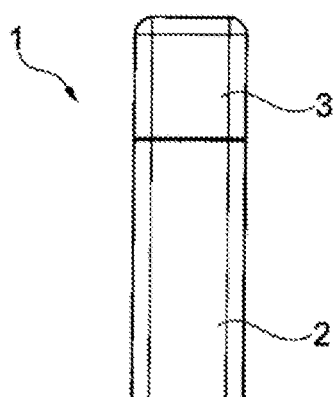

| | | | |
|---|---|---|---|
| 4,401,271 A | 8/1983 | Hansen | |
| 4,450,151 A | 5/1984 | Shinozawa | |
| 4,557,916 A | 12/1985 | Withiam | |
| 4,605,553 A | 8/1986 | Passalacqua | |
| 4,693,925 A | 9/1987 | Cheung et al. | |
| 4,728,571 A | 3/1988 | Clemens et al. | |
| 4,822,596 A | 4/1989 | Callingham et al. | |
| 4,871,529 A | 10/1989 | Sramek | |
| 4,874,554 A | 10/1989 | Lange et al. | |
| 4,957,732 A | 9/1990 | Grollier et al. | |
| 4,972,037 A | 11/1990 | Garbe et al. | |
| 4,983,377 A | 1/1991 | Murphy et al. | |
| 5,297,739 A | 3/1994 | Allen | |
| 5,300,284 A | 4/1994 | Wiechers et al. | |
| 5,508,259 A | 4/1996 | Holzner et al. | |
| 5,538,717 A | 7/1996 | La Poterie | |
| 5,614,173 A | 3/1997 | Ulmer et al. | |
| 5,643,557 A | 7/1997 | Eteve et al. | |
| 5,690,924 A * | 11/1997 | Keil | A61K 8/4913 424/78.03 |
| 5,879,669 A | 3/1999 | Clausen et al. | |
| 5,900,241 A | 5/1999 | Roulier et al. | |
| 6,106,813 A | 8/2000 | Mondet et al. | |
| 6,166,093 A | 12/2000 | Mougin et al. | |
| 6,210,689 B1 | 4/2001 | Martino et al. | |
| 6,245,324 B1 | 6/2001 | Hough et al. | |
| 6,319,959 B1 | 11/2001 | Mougin et al. | |
| 6,350,434 B1 | 2/2002 | Bhatt et al. | |
| 6,372,876 B1 | 4/2002 | Kim et al. | |
| 6,395,265 B1 | 5/2002 | Mougin et al. | |
| 6,415,992 B1 | 7/2002 | Blondeel et al. | |
| 6,589,509 B2 | 7/2003 | Keller et al. | |
| 6,592,854 B1 | 7/2003 | Dupuis | |
| 6,751,886 B2 | 6/2004 | Chang et al. | |
| 7,063,834 B2 | 6/2006 | Mougin et al. | |
| 7,585,824 B2 | 9/2009 | Popplewell et al. | |
| 10,440,140 B2 | 10/2019 | Barraclough et al. | |
| 10,532,880 B2 | 1/2020 | Smail et al. | |
| 2002/0017575 A1 | 2/2002 | Andrews et al. | |
| 2002/0031478 A1 | 3/2002 | Keller et al. | |
| 2002/0150546 A1 | 10/2002 | Mougin et al. | |
| 2003/0150624 A1 | 8/2003 | Rummel | |
| 2003/0150937 A1 | 8/2003 | Laidler et al. | |
| 2003/0163878 A1 | 9/2003 | Pruche | |
| 2003/0185777 A1 | 10/2003 | Banowski et al. | |
| 2003/0191271 A1 | 10/2003 | Mondet et al. | |
| 2004/0047812 A1 | 3/2004 | Pataut et al. | |
| 2004/0170575 A1 | 9/2004 | Belli et al. | |
| 2004/0175404 A1 | 9/2004 | Shefer et al. | |
| 2005/0163737 A1 | 7/2005 | Lemoine et al. | |
| 2005/0220723 A1 | 10/2005 | Benabdillah et al. | |
| 2005/0224524 A1 * | 10/2005 | Khan | C07D 413/06 222/402.13 |
| 2008/0019928 A1 | 1/2008 | Franzke et al. | |
| 2008/0172807 A1 | 7/2008 | Brun | |
| 2008/0274071 A1 | 11/2008 | Kaplan et al. | |
| 2009/0061004 A1 | 3/2009 | Birkel et al. | |
| 2009/0218418 A1 | 9/2009 | Sharief | |
| 2010/0040572 A1 | 2/2010 | Mougin | |
| 2012/0097180 A1 | 4/2012 | Harris et al. | |
| 2012/0171264 A1 | 7/2012 | Bernet et al. | |
| 2012/0258052 A1 | 10/2012 | Mueller et al. | |
| 2012/0282190 A1 | 11/2012 | Hammer | |
| 2013/0289080 A1 | 10/2013 | Masse et al. | |
| 2013/0340786 A1 | 12/2013 | Rodrigues et al. | |
| 2014/0030196 A1 | 1/2014 | Russell et al. | |
| 2014/0079747 A1 | 3/2014 | Dihora et al. | |
| 2015/0014443 A1 | 1/2015 | Albisetti | |
| 2015/0041559 A1 | 2/2015 | Albisetti | |
| 2015/0104397 A1 | 4/2015 | Smail et al. | |
| 2015/0139917 A1 * | 5/2015 | Gawtrey | A61K 8/34 424/46 |
| 2016/0075501 A1 | 3/2016 | Aubert et al. | |
| 2016/0100667 A1 | 4/2016 | Aubert et al. | |
| 2016/0106634 A1 | 4/2016 | Gawtrey et al. | |
| 2018/0000700 A1 | 1/2018 | Smail et al. | |
| 2018/0016087 A1 | 1/2018 | Smail et al. | |
| 2018/0243763 A1 | 8/2018 | Eurippini | |

FOREIGN PATENT DOCUMENTS

| | | | | |
|---|---|---|---|---|
| DE | 102008035013 A1 | 1/2010 | | |
| EP | 0080976 A1 | 6/1983 | | |
| EP | 0095238 A2 | 11/1983 | | |
| EP | 0186507 A2 | 7/1986 | | |
| EP | 0342834 A2 | 11/1989 | | |
| EP | 0412704 A2 | 2/1991 | | |
| EP | 0412707 A1 | 2/1991 | | |
| EP | 0452208 A1 * | 10/1991 | | B05B 7/0062 |
| EP | 0452208 A1 | 10/1991 | | |
| EP | 0530974 A1 | 3/1993 | | |
| EP | 0582152 A2 | 2/1994 | | |
| EP | 0619111 A1 | 10/1994 | | |
| EP | 0637600 A1 | 2/1995 | | |
| EP | 0648485 A1 | 4/1995 | | |
| EP | 0751162 A1 | 1/1997 | | |
| EP | 0974332 A1 | 1/2000 | | |
| EP | 1026220 A1 | 8/2000 | | |
| EP | 1407754 A1 | 4/2004 | | |
| EP | 2444160 A1 | 4/2012 | | |
| EP | 2777770 A1 | 9/2014 | | |
| FR | 1222944 A | 6/1960 | | |
| FR | 1400366 A | 5/1965 | | |
| FR | 1564110 A | 4/1969 | | |
| FR | 1578989 A | 8/1969 | | |
| FR | 1580545 A | 9/1969 | | |
| FR | 1600138 A | 7/1970 | | |
| FR | 2077143 A5 | 10/1971 | | |
| FR | 2198719 A1 | 4/1974 | | |
| FR | 2265781 A1 | 10/1975 | | |
| FR | 2265782 A1 | 10/1975 | | |
| FR | 2350384 A1 | 12/1977 | | |
| FR | 2357241 A2 | 2/1978 | | |
| FR | 2393573 A1 | 1/1979 | | |
| FR | 2434194 A1 | 3/1980 | | |
| FR | 2439798 A1 | 5/1980 | | |
| FR | 2589476 A1 | 5/1987 | | |
| FR | 2715841 A1 | 8/1995 | | |
| FR | 2743297 A1 | 7/1997 | | |
| FR | 2814943 A1 | 4/2002 | | |
| FR | 2924341 A1 | 6/2009 | | |
| FR | 2980125 A1 | 3/2013 | | |
| FR | 2985201 A1 | 7/2013 | | |
| FR | 2985202 A1 | 7/2013 | | |
| FR | 2990131 A1 | 11/2013 | | |
| FR | 2990133 A1 | 11/2013 | | |
| FR | 3004901 A1 | 10/2014 | | |
| FR | 3004902 A1 | 10/2014 | | |
| FR | 3004929 A1 | 10/2014 | | |
| FR | 3031437 A1 | 7/2016 | | |
| GB | 839805 A | 6/1960 | | |
| GB | 922457 A | 4/1963 | | |
| GB | 1021400 A | 3/1966 | | |
| GB | 1218222 A | 1/1971 | | |
| GB | 1235908 A | 6/1971 | | |
| GB | 1331819 A | 9/1973 | | |
| GB | 1408388 A | 10/1975 | | |
| GB | 1572626 A | 7/1980 | | |
| GB | 2340891 A * | 3/2000 | | B65D 83/205 |
| GB | 2340891 A | 3/2000 | | |
| JP | 2003-326197 A | 11/2003 | | |
| JP | 2011-213619 A | 10/2011 | | |
| LU | 75370 A1 | 2/1978 | | |
| LU | 75371 A1 | 2/1978 | | |
| WO | 93/23009 A1 | 11/1993 | | |
| WO | 94/03510 A1 | 2/1994 | | |
| WO | 95/00578 A1 | 1/1995 | | |
| WO | 98/43599 A1 | 10/1998 | | |
| WO | 02/078653 A1 | 10/2002 | | |
| WO | 02/096379 A1 | 12/2002 | | |
| WO | 03/045573 A1 | 6/2003 | | |
| WO | 03/049711 A2 | 6/2003 | | |
| WO | 2004/043608 A1 | 5/2004 | | |
| WO | 2011/019539 A2 | 2/2011 | | |

(56) References Cited

FOREIGN PATENT DOCUMENTS

| | | |
|---|---|---|
| WO | 2011/056625 A1 | 5/2011 |
| WO | 2012/035053 A1 | 3/2012 |
| WO | 2012/080255 A2 | 6/2012 |
| WO | 2013/064918 A1 | 5/2013 |
| WO | 2013/167530 A2 | 11/2013 |
| WO | 2013/167536 A2 | 11/2013 |
| WO | 2014/177646 A2 | 11/2014 |
| WO | 2014/177647 A1 | 11/2014 |
| WO | 2014/177649 A1 | 11/2014 |
| WO | 2016/001190 A1 | 1/2016 |
| WO | 2016/005703 A1 | 1/2016 |
| WO | 2016/066729 A1 | 5/2016 |
| WO | 2016/066730 A1 | 5/2016 |
| WO | 2016/092109 A1 | 6/2016 |
| WO | 2016/110575 A1 | 7/2016 |
| WO | 2016/110578 A1 | 7/2016 |
| WO | 2016/110579 A1 | 7/2016 |
| WO | 2018/162701 A1 | 9/2018 |
| WO | 2018/162711 A1 | 9/2018 |

OTHER PUBLICATIONS

Porter, M.R., "Handbook of Surfactants," published by Blackie & Son (Glasgow and London), 1991, pp. 116-178.
Mintel: "Styling Mousse," Nov. 2008, XP002736036.
Non-Final Office Action for copending U.S. Appl. No. 14/888,013, dated Mar. 14, 2019.
Mintel: "Clean Freak Refreshing Dry Shampoo," XP007923188, Demert Brands, Mar. 2014.
Final Office Action for U.S. Appl. No. 14/399,764, dated Jun. 7, 2019 (now abandoned).
Notice of Allowance for U.S. Appl. No. 15/523,242, dated Jun. 12, 2019 (now U.S. Pat. No. 10,449,140).
Non-Final Office Action for copending U.S. Appl. No. 14/787,983, dated Jun. 26, 2019.
Final Office Action for copending U.S. Appl. No. 15/541,741, dated Jul. 11, 2019.
Notice of Allowance for U.S. Appl. No. 15/541,738, dated Sep. 4, 2019 (now U.S. Pat. No. 10,532,880).
Supplemental Notice of Allowance for U.S. Appl. No. 15/523,242, dated Sep. 5, 2019 (now U.S. Pat. No. 10,449,140).
Non-Final Office Action for copending U.S. Appl. No. 15/322,771, dated Sep. 6, 2019.
Non-Final Office Action for U.S. Appl. No. 15/324,804, dated Oct. 10, 2019 (now abandoned).
Final Office Action for copending U.S. Appl. No. 14/888,013, dated Oct. 18, 2019.
Non-Final Office Action for copending U.S. Appl. No. 14/888,002, dated Oct. 7, 2019.
Non-Final Office Action for U.S. Appl. No. 15/541,743, dated Nov. 21, 2019 (now U.S. Pat. No. 10,710,791).
Non-Final Office Action for copending U.S. Appl. No. 15/523,232, dated Feb. 20, 2020.
Final Office Action for copending U.S. Appl. No. 14/787,983, dated Feb. 26, 2020.
Non-Final Office Action for copending U.S. Appl. No. 15/541,741, dated Mar. 3, 2020.
ClearCo, "Cyclo-1400-DM D5 Cyclomethicone/dimethicone blend," ([retrieved from on-line website: http://www.clearcoproducts.com/cyclo-1400-d5-blend.html], 2013, pp. 1-2.
Wayback Machine to support publication year of ClearCo (Year: 2013).
Notice of Allowance for U.S. Appl. No. 15/541,743, dated Mar. 18, 2020 (now U.S. Pat. No. 10,710,791).
Non-Final Office Action for copending U.S. Appl. No. 15/322,771, dated Mar. 20, 2020.
Final Office Action for U.S. Appl. No. 15/324,804, dated Apr. 20, 2020 (now abandoned).
Final Office Action for copending U.S. Appl. No. 14/888,002, dated Jun. 1, 2020.
Final Office Action for copending U.S. Appl. No. 15/322,771, dated Jul. 10, 2020.
Non-Final Office Action for copending U.S. Appl. No. 14/787,983, dated Jul. 15, 2020.
Final Office Action of copending U.S. Appl. No. 15/541,741, dated Sep. 17, 2020.
Final Office Action for copending U.S. Appl. No. 15/523,232, dated Oct. 1, 2020.
Final Office Action for copending U.S. Appl. No. 14/787,983, dated Feb. 19, 2021.
Non-Final Office Action for copending U.S. Appl. No. 15/322,771, dated Mar. 2, 2021.
Non-Final Office Action for copending U.S. Appl. No. 14/888,013, dated May 11, 2021.
Final Office Action for U.S. Appl. No. 13/993,413, dated Dec. 30, 2015 (now abandoned).
Non-Final Office Action for U.S. Appl. No. 13/993,413, dated Nov. 8, 2017 (now abandoned).
Final Office Action for U.S. Appl. No. 13/993,413, dated Jul. 5, 2018 (now abandoned).
Final Office Action for U.S. Appl. No. 15/324,804, dated Nov. 30, 2018 (now abandoned).
Non-Final Office Action for copending U.S. Appl. No. 15/541,741, dated May 27, 2021.
International Search Report for counterpart Application No. PCT/EP2013/059382, dated Jun. 20, 2014.
International Search Report for counterpart Application No. PCT/EP2013/059393, dated Jun. 20, 2014.
Database WPI Week 201172, Thomas Scientific, London, GB, AN 2011-N36295, XP002690571 (Jan. 25, 2013).
Mintel: Apr. 2010, "Refresh Dry Shampoo".
Mintel: Jun. 2011, "Brown Hair Powder Shampoo".
Oscar Blandi, http://www.skinstore.com/p-6885-oscar-blandi-pronto-dry-shampoo-spray.aspx. Published Jun. 13, 2011.
Non-Final Office Action for U.S. Appl. No. 14/399,753, dated Sep. 8, 2015 (now abandoned).
Final Office Action for U.S. Appl. No. 14/399,753, dated Mar. 30, 2016 (now abandoned).
Non-Final Office Action for U.S. Appl. No. 14/399,764, dated Dec. 17, 2015 (now abandoned).
International Search Report for counterpart Application No. PCT/EP2014/058896, dated Sep. 23, 2014.
International Search Report and Written Opinion for counterpart Application No. PCT/EP2014/058892, dated Oct. 29, 2014.
International Search Report for counterpart Application No. PCT/EP2014/058894, dated Sep. 29, 2014.
Oxford Dictionary, Half-Ester, http://www.oxfordreference.com/view/10.1093/acref/9780198529170.001.0001/acref-9780198529170-e-8589, retrieved online on Oct. 19, 2017 (Year:2017).
Final Office Action for U.S. Appl. No. 14/399,764, dated Aug. 5, 2016 (now abandoned).
Non-Final Office Action for copending U.S. Appl. No. 14/888,002, dated Sep. 9, 2016.
Non-Final Office Action for copending U.S. Appl. No. 14/787,983, dated Sep. 15, 2016.
Final Office Action for U.S. Appl. No. 14/399,753, dated Sep. 30, 2016 (now abandoned).
Non-Final Office Action for copending U.S. Appl. No. 14/888,013, dated Apr. 13, 2017.
Non-Final Office Action for U.S. Appl. No. 14/399,764, dated Mar. 8, 2017 (now abandoned).
Final Office Action for copending U.S. Appl. No. 14/787,983, dated May 30, 2017.
International Search Report for counterpart Application No. PCT/FR2015/051896, dated Oct. 19, 2015 (now abandoned).
International Search Report for counterpart Application No. PCT/EP2015/075061, dated Jan. 20, 2016.
International Search Report for counterpart Application No. PCT/EP2015/075062, dated Jan. 26, 2016.
Mintel: "Code 10 Hair Styling Cream," XP007923186, Sep. 2001.
Mintel: "One More Day Dry Shampoo," XP007923187, Aug. 2013.
Mintel: "Foot Deodorant Spray," XP007923193, Oct. 2013.
Mintel: "72h Anti-Perspirant Deodorant," XP007923192, Jan. 2014.

(56) References Cited

OTHER PUBLICATIONS

Mintel: "Dry Shampoo," XP007923191, Jan. 2014.
Non-Final Office Action for U.S. Appl. No. 15/324,804, dated Mar. 5, 2018 (now abandoned).
Non-Final Office Action for copending U.S. Appl. No. 15/523,232, dated Feb. 23, 2018.
Bezard et al., "Triglyceride Composition of Coconut Oil," Journal of American Oil Chemists' Society, 48, 3, Mar. 1971, pp. 134-139.
Non-Final Office Action for U.S. Appl. No. 15/523,242, dated Aug. 31, 2017 (now U.S. Pat. No. 10,449,140).
Final Office Action for copending U.S. Appl. No. 14/888,013, dated Aug. 15, 2017.
Final Office Action for copending U.S. Appl. No. 14/888,002, dated Sep. 21, 2017.
Final Office Action for U.S. Appl. No. 14/399,764, dated Aug. 16, 2017 (now abandoned).
Non-Final Office Action for U.S. Appl. No. 14/399,753, dated Oct. 4, 2017 (now abandoned).
Non-Final Office Action for copending U.S. Appl. No. 14/787,983, dated May 11, 2018.
Non-Final Office Action for U.S. Appl. No. 15/523,242, dated Mar. 27, 2018 (now abandoned).
International Search Report for counterpart Application No. PCT/EP2011/072617, dated Jul. 5, 2012 (now abandoned).
Todd, Charles, et al., "Volatile Silicone Fluids for Cosmetic Formulations," Cosmetics and Toiletries, vol. 91, Jan. 1976, pp. 29-32.
International Search Report for counterpart Application No. PCT/EP2016/050295, dated Mar. 23, 2016 (now U.S. Pat. No. 10,532,880).
International Search Report for counterpart Application No. PCT/EP2016/050299, dated Mar. 23, 2016.
International Search Report for counterpart Application No. PCT/EP2016/0503300, dated Mar. 16, 2016 (now U.S. Pat. No. 10,710,791).
Non-Final Office Action for U.S. Appl. No. 15/541,738, dated May 17, 2018 (now U.S. Pat. No. 10,532,880).
Non-Final Office Action for U.S. Appl. No. 13/993,413, dated May 19, 2015 (now abandoned).
Oxford Dictionary of Biochemistry and Molecular Biology (2 ed.), Half-Ester, http://www.oxfordreference.com/view/10.1093/acref/9780198529170.001.0001/acref-9780198529170-e-8589, retrieved online on Oct. 19, 2017 (Year:2017).
International Search Report and Written Opinion for counterpart Application No. PCT/EP2018/055882, dated May 4, 2018.
International Search Report and Written Opinion for counterpart Application No. PCT/EP2018/055889, dated May 4, 2018.
International Search Report and Written Opinion for counterpart Application No. PCT/EP2018/055904, dated Apr. 30, 2018.
Brunauer et al., "Adsorption of Gases in Multimolecular Layers," Journal of the American Chemical Society, vol. 60, Feb. 1938, pp. 309-319.
Non-Final Office Action for copending U.S. Appl. No. 16/491,375, dated Nov. 25, 2019.
Final Office Action for copending U.S. Appl. No. 16/491,375, dated May 26, 2020.
Non-Final Office Action for copending U.S. Appl. No. 16/491,372, dated May 28, 2020.
NPL Search String: IQQueryQuickExport 202005221756, downloaded May 22, 2020.
NPL Search String: IQQueryQuickExport 202005221759, downloaded May 22, 2020.
Final Office Action for copending U.S. Appl. No. 16/491,372, dated Dec. 18, 2020.
Non-Final Office Action for copending U.S. Appl. No. 16/491,372, dated Jul. 12, 2021.
Non-Final Office Action for copending U.S. Appl. No. 14/888,002, dated Sep. 3, 2021.
Final Office Action for copending U.S. Appl. No. 14/888,013, dated Sep. 3, 2021.
Non-Final Office Action for copending U.S. Appl. No. 16/491,374, dated Oct. 20, 2021.

\* cited by examiner

AEROSOL DEVICE FOR HAIR SHAPING AND/OR HAIRSTYLE HOLD

CROSS REFERENCE TO RELATED APPLICATIONS

This is a national stage application of PCT/EP2018/055889, filed internationally on Mar. 9, 2018, which claims priority to French Application No. 1751945, filed on Mar. 9, 2017, both of which are incorporated by reference herein in their entireties.

The present invention relates to an aerosol device comprising a particular dispensing means and a composition based on at least one fixing polymer, and to a process for treating the hair, especially for shaping the hair and/or holding the hairstyle.

The hair products for shaping and/or holding the hairstyle that are the most widespread on the cosmetics market are spray compositions, such as lacquers and sprays or compositions dispensed in the form of foams. They essentially consist of an alcoholic or aqueous solution and of one or more materials, generally polymeric resins, also referred to as fixing polymers, whose function is to form welds between the individual hairs or to coat the hairs, as a mixture with various cosmetic adjuvants.

These products provide fixing and hold of the hairstyle over time. In practice, however, these products are not entirely satisfactory, especially in terms of the cosmetic qualities on the hair. The aerosol sprays conventionally used which generate a spray or a foam, when applied to all or part of the hair, are liable to create fibre irregularities along an individual hair on account of the diffusion of the spray in the form of droplets or by spreading of the foam.

Aerosol devices comprising three outlet orifices have already been proposed for dispensing shaping products, especially in patent application EP 2 991 735, the three orifices spraying the composition in the same direction.

Patent application US 2002/0017575 describes a spray device comprising one or more spray stems pierced with orifices allowing a product to be diffused in the hair.

There is a need to develop a new aerosol device comprising a hair shaping composition which can afford good shaping of the hairstyle while at the same time obtaining a good level of cosmeticity.

The Applicant has found, surprisingly and advantageously, that the use of a device equipped with a dispensing head comprising at least two outlet orifices for spraying the composition in at least two different directions and at least two chambers through which the composition stream successively passes before it exits via the outlet orifices to dispense a composition comprising a fixing polymer allows a hairstyle to be shaped easily and quickly, with satisfactory and long-lasting volume.

The changes of direction of the composition stream in the dispensing head create turbulences in the composition stream, which produces good-quality sprays.

According to a first of its aspects, a subject of the invention is an aerosol device comprising:

a container containing a cosmetic composition which comprises at least one fixing polymer, and a dispensing head comprising a body and an end part comprising at least two outlet orifices configured to allow spraying of the composition about a longitudinal axis of the end part in at least two different directions, the dispensing head comprising at least first and second concentric chambers through which the composition stream successively passes before it exits via the outlet orifices, the dispensing head comprising at least one aperture between the first and second concentric chambers which is angularly offset relative to at least one of the outlet orifices.

This particular combination makes it possible mainly to apply the product at the root, thus improving the cosmetic qualities of the hair after application by maintaining a natural non-rigid effect while at the same time obtaining satisfactory volume.

The present invention also relates to a process for treating the hair, especially for shaping the hair and/or holding the hairstyle, comprising the use of the device as defined previously. In particular, the hair treatment process comprises a step of applying, to dry or wet hair, a composition sprayed from an aerosol device according to the invention, optionally to be rinsed off after an optional leave-on time or after optional drying.

Other subjects, characteristics, aspects and advantages of the invention will emerge even more clearly on reading the description and the example that follows.

In the text hereinbelow, and unless otherwise indicated, the limits of a range of values are included within that range, especially in the expressions "between" and "ranging from . . . to . . . ".

Moreover, the expression "at least one" used in the present description is equivalent to the expression "one or more".

According to the invention, the aerosol device comprises a container which contains a composition comprising one or more fixing polymers.

For the purposes of the invention, the term "fixing polymer" means any polymer that is capable, by application to the hair, of giving a shape to a head of hair or of holding the hair in an already acquired shape.

The fixing polymer(s) used are chosen from ionic, especially anionic, cationic or amphoteric, and nonionic fixing polymers, and mixtures thereof.

Anionic polymers that may be mentioned include polymers comprising groups derived from carboxylic, sulfonic or phosphoric acids, and having a number-average molecular mass of between 500 and 5 000 000.

The carboxylic groups are provided by unsaturated monocarboxylic or dicarboxylic acid monomers, such as those corresponding to the formula:

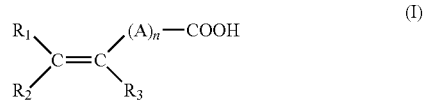

(I)

in which n is an integer from 0 to 10, A denotes a methylene group which is optionally connected to the carbon atom of the unsaturated group or to the neighbouring methylene group when n is greater than 1, via a heteroatom such as oxygen or sulfur, $R_1$ denotes a hydrogen atom or a phenyl or benzyl group, $R_2$ denotes a hydrogen atom, an alkyl group containing from 1 to 4 carbon atoms, or a carboxyl group, $R_3$ denotes a hydrogen atom, an alkyl group containing from 1 to 4 carbon atoms, or a —$CH_2$—COOH, phenyl or benzyl group.

In formula (I) above, the alkyl group containing from 1 to 4 carbon atoms may in particular denote methyl and ethyl groups.

The anionic fixing polymers bearing carboxylic or sulfonic groups that are preferred are:

A) Copolymers of acrylic or methacrylic acid or salts thereof, including copolymers of acrylic acid and acrylamide, and methacrylic acid/acrylic acid/ethyl acrylate/methyl methacrylate copolymers, more particularly Amerhold DR 25 sold by the company Amerchol, and sodium salts of polyhydroxycarboxylic acids. Mention may also be made of methacrylic acid/ethyl acrylate copolymers, in particular in aqueous dispersion, such as Luviflex Soft and Luvimer MAE, which are sold by the company BASF.

B) Copolymers of acrylic or methacrylic acids with a monoethylenic monomer such as ethylene, styrene, vinyl esters and acrylic or methacrylic acid esters, optionally grafted onto a polyalkylene glycol such as polyethylene glycol and optionally crosslinked. Such polymers are described in particular in French patent 1 222 944 and German patent application No. 2 330 956, the copolymers of this type comprising an optionally N-alkylated and/or hydroxyalkylated acrylamide unit in their chain as described especially in Luxembourg patent applications 75370 and 75371. Mention may also be made of copolymers of acrylic acid and $C_1$-$C_4$ alkyl methacrylate.

As another anionic fixing polymer from this class, mention may also be made of the branched sequenced anionic butyl acrylate/acrylic acid/methacrylic acid polymer sold under the name Fixate G-100 L by the company Lubrizol (INCI name AMP-Acrylates/Allyl Methacrylate Copolymer).

C) Copolymers derived from crotonic acid, such as those comprising, in their chain, vinyl propionate or acetate units, and optionally other monomers such as allyl or methallyl esters, vinyl ethers or vinyl esters of a linear or branched, saturated carboxylic acid with a long hydrocarbon-based chain, such as those comprising at least 5 carbon atoms, it being possible for these polymers optionally to be grafted and crosslinked, or else a vinyl, allyl or methallyl ester of an α- or β-cyclic carboxylic acid. Such polymers are described, inter alia, in French patents Nos. 1 222 944, 1 580 545, 2 265 782, 2 265 781, 1 564 110 and 2 439 798. Commercial products that fall within this category are the resins 28-29-30, 26-13-14 and 28-13-10 sold by National Starch.

Mention may also be made, as copolymer derived from crotonic acid, of crotonic acid/vinyl acetate/vinyl tert-butyl-benzoate terpolymers, and in particular Mexomer PW supplied by the company Chimex.

D) Polymers derived from maleic, fumaric or itaconic acids or anhydrides with vinyl esters, vinyl ethers, vinyl halides, phenylvinyl derivatives or acrylic acid and esters thereof; these polymers may be esterified. Such polymers are described in particular in U.S. Pat. Nos. 2,047,398, 2,723,248 and 2,102,113 and GB patent 839 805, and especially those sold under the names Gantrez® AN or ES by ISP.

Polymers also falling into this category are the copolymers of maleic, citraconic or itaconic anhydrides and of an allyl or methallyl ester optionally comprising an acrylamide or methacrylamide group, an α-olefin, acrylic or methacrylic esters, acrylic or methacrylic acids or vinylpyrrolidone in their chain, the anhydride functions being monoesterified or monoamidated. These polymers are described, for example, in French patents 2 350 384 and 2 357 241 by the Applicant.

E) Polyacrylamides comprising carboxylate groups.

F) Polymers containing sulfonic groups. These polymers may be polymers comprising vinylsulfonic, styrenesulfonic, naphthalenesulfonic, acrylamidoalkylsulfonic or sulfoisophthalate units.

These polymers may be chosen especially from:

polyvinylsulfonic acid salts having a molecular mass of between approximately 1000 and 100 000, and also copolymers with an unsaturated comonomer, such as acrylic or methacrylic acids and esters thereof, and also acrylamide or derivatives thereof, vinyl ethers and vinylpyrrolidone;

polystyrenesulfonic acid salts and sodium salts, having a molecular mass of approximately 500 000 and of about 100 000. These compounds are described in patent FR 2198719;

polyacrylamidesulfonic acid salts such as those mentioned in patent U.S. Pat. No. 4,128,631;

G) Grafted anionic silicone polymers.

The grafted silicone polymers used are preferably chosen from polymers containing a non-silicone organic backbone grafted with monomers containing a polysiloxane, polymers containing a polysiloxane backbone grafted with non-silicone organic monomers, and mixtures thereof.

H) Anionic polyurethanes, possibly comprising silicone grafts and silicones containing hydrocarbon-based grafts.

Examples of fixing polyurethanes that may especially be mentioned include the dimethylolpropionic acid/isophorone diisocyanate/neopentyl glycol/polyester diols copolymer (also known under the name polyurethane-1, INCI name) sold under the brand name Luviset® PUR by the company BASF, and the dimethylolpropionic acid/isophorone diisocyanate/neopentyl glycol/polyester diols/silicone diamine copolymer (also known under the name polyurethane-6, INCI name) sold under the brand name Luviset® Si PUR A by the company BASF.

Another anionic polyurethane that may also be used is Avalure UR 450.

Polymers containing sulfoisophthalate groups, such as the polymers AQ55 and AQ48 sold by the company Eastman, may also be used.

According to the invention, the anionic polymers are preferably selected from copolymers of acrylic acid such as the acrylic acid/ethyl acrylate/N-tert-butylacrylamide terpolymer sold under the name Ultrahold Strong® or Ultrahold Power® by the company BASF, and methacrylic acid/ethyl acrylate copolymers, especially in aqueous dispersion, such as Luviflex Soft and Luvimer MAE, which are sold by the company BASF. Copolymers derived from crotonic acid such as vinyl acetate/vinyl tert-butylbenzoate/ crotonic acid terpolymers and crotonic acid/vinyl acetate/ vinyl neododecanoate terpolymers, which are sold under the name Resin 28-2930 by the company Akzo Nobel, polymers derived from maleic, fumaric or itaconic acids or anhydrides with vinyl esters, vinyl ethers, vinyl halides, phenylvinyl derivatives, acrylic acid and its esters, such as the monoesterified maleic anhydride/methyl vinyl ether copolymer sold under the name Gantrez® ES 425 by the company ISP, Luviset SI PUR, Mexomere PW, elastomeric or non-elastomeric anionic polyurethanes, and polymers containing sulfoisophthalate groups.

The cationic fixing polymers that may be used according to the present invention are preferably chosen from polymers comprising primary, secondary, tertiary and/or quaternary amine groups forming part of the polymer chain or directly attached thereto, and having a molecular weight of between 500 and approximately 5 000 000 and preferably between 1000 and 3 000 000.

Among these polymers, mention may be made more particularly of the following cationic polymers:

(1) Homopolymers or copolymers derived from acrylic or methacrylic esters or amides and comprising at least one of the units of following formulae:

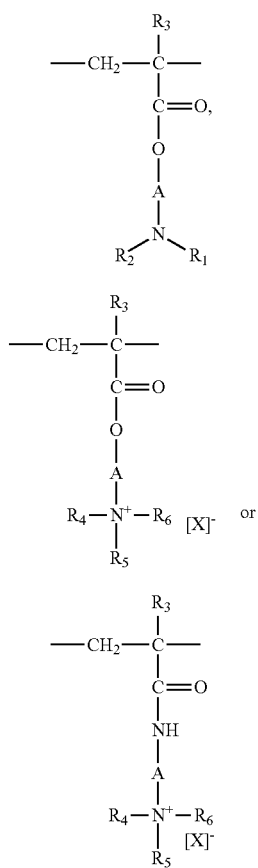

in which:

R₃ denotes a hydrogen atom or a CH₃ group;

A is a linear or branched alkyl group comprising from 1 to 6 carbon atoms or a hydroxyalkyl group comprising from 1 to 4 carbon atoms;

$R_4$, $R_5$ and $R_6$, which may be identical or different, represent an alkyl group containing from 1 to 18 carbon atoms, or a benzyl group;

$R_1$ and $R_2$, which may be identical or different, each represent a hydrogen atom or an alkyl group containing from 1 to 6 carbon atoms;

X denotes a methosulfate anion or a halide such as chloride or bromide.

The copolymers of class (1) also contain one or more units derived from comonomers which may be chosen from the class of acrylamides, methacrylamides, diacetone acrylamides, acrylamides and methacrylamides substituted on the nitrogen with $C_1$-$C_4$ alkyl groups, groups derived from acrylic or methacrylic acids or esters thereof, vinyllactams such as vinylpyrrolidone or vinylcaprolactam, and vinyl esters.

Thus, mention may be made, among these copolymers of class (1), of:

copolymers of acrylamide and of dimethylaminoethyl methacrylate which is quaternized with dimethyl sulfate or with a dimethyl halide, such as that sold under the name Hercofloc® by the company Hercules, copolymers of acrylamide and methacryloyloxyethyltrimethylammonium chloride, described for example in patent application EP-A-080976 and sold under the name Bina Quat P 100 by the company Ciba Geigy, the copolymer of acrylamide and of methacryloyloxyethyltrimethylammonium methosulfate, such as the product sold under the name Reten by the company Hercules, quaternized or non-quaternized vinylpyrrolidone/dialkylaminoalkyl acrylate or methacrylate copolymers, such as the products sold under the name Gafquat® by the company ISP, for instance Gafquat® 734 or Gafquat® 755, or alternatively the products known as Copolymer® 845, 958 and 937. These polymers are described in detail in French patents 2 077 143 and 2 393 573, polymers comprising a fatty chain and comprising a vinylpyrrolidone unit, such as the products sold under the names Styleze W20 and Styleze W10 by the company ISP, dimethylaminoethyl methacrylate/vinylcaprolactam/vinylpyrrolidone terpolymers, such as the product sold under the name Gaffix VC 713 by the company ISP, and quaternized vinylpyrrolidone/dimethylaminopropylmethacrylamide copolymers, such as the products sold under the name Gafquat® HS 100 by the company ISP.

(2) Cationic guar gums, preferably containing quaternary ammonium, such as those described in U.S. Pat. Nos. 3,589,578 and 4,031,307, such as guar gums containing trialkylammonium cationic groups. Such products are sold in particular under the trade names Jaguar C13 S, Jaguar C 15 and Jaguar C 17 by the company Meyhall.

(3) Quaternary copolymers of vinylpyrrolidone and of vinylimidazole.

(4) Chitosans or salts thereof; the salts that may be used are in particular the acetate, lactate, glutamate, gluconate or pyrrolidonecarboxylate of chitosan.

Among these compounds, mention may be made of chitosan having a degree of deacetylation of 90.5% by weight, sold under the name Kytan Brut Standard by the company Aber Technologies, and chitosan pyrrolidonecarboxylate sold under the name Kytamer® PC by the company Amerchol.

(5) Cationic cellulose derivatives such as copolymers of cellulose or of cellulose derivatives grafted with a water-soluble monomer comprising a quaternary ammonium, and disclosed in particular in patent U.S. Pat. No. 4,131,576, such as hydroxyalkylcelluloses, for instance hydroxymethyl-, hydroxyethyl- or hydroxypropylcelluloses grafted in particular with a methacryloyloxyethyltrimethylammonium, methacrylamidopropyltrimethylammonium or dimethyldiallylammonium salt.

The commercial products corresponding to this definition are more particularly the products sold under the names Celquat L 200 and Celquat H 100 by the company National Starch.

The amphoteric fixing polymers that can be used in accordance with the invention may be chosen from polymers comprising units B and C distributed randomly in the polymer chain, in which B denotes a unit deriving from a monomer comprising at least one basic nitrogen atom and C denotes a unit deriving from an acid monomer comprising one or more carboxylic or sulfonic groups, or alternatively B and C may denote groups deriving from carboxybetaine or sulfobetaine zwitterionic monomers; B and C can also denote a cationic polymer chain comprising primary, secondary, tertiary or quaternary amine groups, in which at least one of the amine groups bears a carboxylic or sulfonic group connected via a hydrocarbon-based group, or alternatively B and C form part of a chain of a polymer containing an ethylenedicarboxylic unit in which one of the carboxylic groups has been made to react with a polyamine comprising one or more primary or secondary amine groups.

The amphoteric polymers corresponding to the definition given above that are more particularly preferred are chosen from the following polymers:

1) Polymers resulting from the copolymerization of a monomer derived from a vinyl compound bearing a carboxylic group, such as, more particularly, acrylic acid, methacrylic acid, maleic acid, α-chloroacrylic acid, and a basic monomer derived from a substituted vinyl compound containing at least one basic atom, such as, more particularly, dialkylaminoalkyl methacrylate and acrylate, dialkylaminoalkyl methacrylamide and acrylamide. Such compounds are described in U.S. Pat. No. 3,836,537.

The vinyl compound may also be a dialkyldiallylammonium salt such as diethyldiallylammonium chloride.

2) Polymers containing units derived:
a) from at least one monomer chosen from acrylamides or methacrylamides which are substituted on the nitrogen by an alkyl group,
b) from at least one acidic comonomer containing one or more reactive carboxylic groups, and
c) from at least one basic comonomer such as acrylic and methacrylic acid esters containing primary, secondary, tertiary and quaternary amine substituents, and the product of quaternization of dimethylaminoethyl methacrylate with dimethyl or diethyl sulfate.

The N-substituted acrylamides or methacrylamides that are more particularly preferred according to the invention are compounds in which the alkyl groups contain from 2 to 12 carbon atoms and more particularly N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers are more particularly chosen from acrylic acid, methacrylic acid, crotonic acid, itaconic acid, maleic acid and fumaric acid and alkyl monoesters, containing 1 to 4 carbon atoms, of maleic or fumaric acids or anhydrides. The preferred basic comonomers are aminoethyl, butylaminoethyl, N,N'-dimethylaminoethyl and N-tert-butylaminoethyl methacrylates. The copolymers of which the CTFA (4th edition, 1991) name is octylacrylamide/acrylates/butylaminoethyl methacrylate copolymer, such as the products sold under the name Amphomer® or Lovocryl® 47 by the company National Starch, are particularly used.

3) Crosslinked and alkylated polyamino amides partially or totally derived from polyamino amides of general formula:

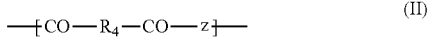

(II)

in which $R_4$ represents a divalent group derived from a saturated dicarboxylic acid, from a mono- or dicarboxylic aliphatic acid with an ethylenic double bond, from an ester of an alcohol containing 1 to 6 carbon atoms with these acids, or from a group deriving from the addition of any one of said acids with a bis-primary amine or bis-secondary-derived amine, and Z denotes a group of a bis-primary or mono- or bis-secondary polyalkylene-polyamine, and preferably represents:

a) in proportions of from 60 mol % to 100 mol %, the group

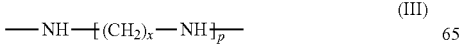

(III)

where x=2 and p=2 or 3, or else x=3 and p=2, this group being derived from diethylenetriamine, from triethylenetramine or from dipropylenetriamine;

b) in proportions of from 0 to 40 mol %, the group (Ill) above, in which x=2 and p=1, which derives from ethylenediamine, or the group deriving from piperazine

c) in proportions of from 0 to 20 mol %, the —NH—(CH2)6-NH— group being derived from hexamethylenediamine, these polyamino amines being crosslinked by addition of a difunctional crosslinking agent chosen from epihalohydrins, diepoxides, dianhydrides and bis-unsaturated derivatives, using from 0.025 to 0.35 mol of crosslinking agent per amine group of the polyamino amide and alkylated by the action of acrylic acid, chloroacetic acid or an alkane sultone, or salts thereof.

The saturated carboxylic acids are preferably chosen from acids containing 6 to 10 carbon atoms, such as adipic acid, 2,2,4-trimethyladipic acid, 2,4,4-trimethyladipic acid and terephthalic acid, and acids bearing an ethylenic double bond, for instance acrylic, methacrylic and itaconic acids. The alkane sultones used in the alkylation are preferably propane sultone or butane sultone, the salts of the alkylating agents are preferably the sodium or potassium salts.

4) Polymers containing zwitterionic units of formula:

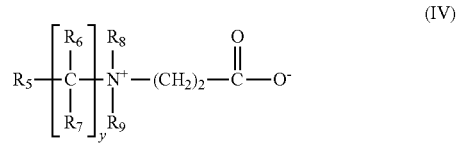

(IV)

in which $R_5$ denotes a polymerizable unsaturated group, such as an acrylate, methacrylate, acrylamide or methacrylamide group, y and z each represent an integer from 1 to 3, $R_6$ and $R_7$ represent a hydrogen atom or a methyl, ethyl or propyl group, $R_8$ and $R_9$ represent a hydrogen atom or an alkyl group such that the sum of the carbon atoms in $R_{10}$ and $R_{11}$ does not exceed 10.

The polymers comprising such units may also comprise units derived from non-zwitterionic monomers such as dimethyl- or diethylaminoethyl acrylate or methacrylate or alkyl acrylates or methacrylates, acrylamides or methacrylamides or vinyl acetate.

5) Polymers derived from chitosan comprising monomer units corresponding to the following formulae:

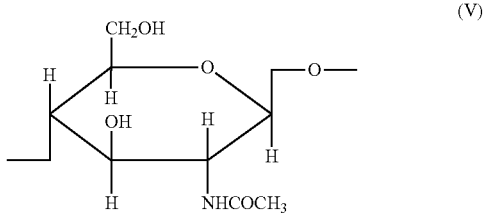

(V)

-continued

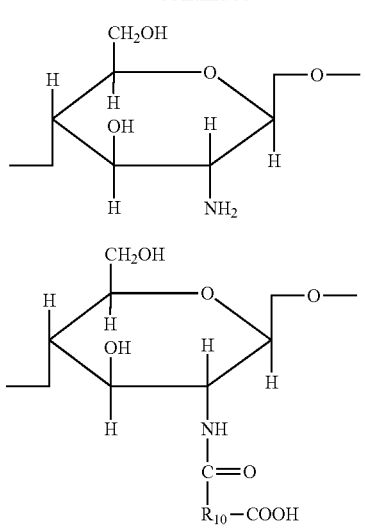

the unit (V) being present in proportions of between 0 and 30%, the unit (VI) in proportions of between 5% and 50% and the unit (VII) in proportions of between 30% and 90%, it being understood that, in this unit F, $R_{10}$ represents a group of formula:

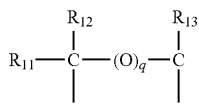

in which, if q=0, $R_{11}$, $R_{12}$ and $R_{13}$, which may be identical or different, each represent a hydrogen atom, a methyl, hydroxyl, acetoxy or amino residue, a monoalkylamine residue or a dialkylamine residue that are optionally interrupted with one or more nitrogen atoms and/or optionally substituted with one or more amine, hydroxyl, carboxyl, alkylthio or sulfonic groups, an alkylthio residue in which the alkyl group bears an amino residue, at least one of the groups $R_{17}$, $R_{18}$ and $R_{19}$ being, in this case, a hydrogen atom;

or, if q=1, $R_{11}$, $R_{12}$ and $R_{13}$ each represent a hydrogen atom, and also the salts formed by these compounds with bases or acids.

6) Polymers derived from the N-carboxyalkylation of chitosan.

7) Polymers of units corresponding to general formula (IX), described, for example, in French patent 1 400 366:

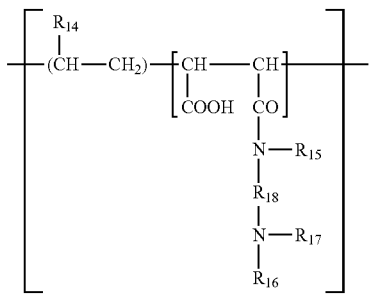

in which $R_{14}$ represents a hydrogen atom or a $CH_3O$, $CH_3CH_2O$, or phenyl group, $R_{15}$ denotes hydrogen or a $C_1$-$C_4$ alkyl group such as methyl and ethyl, $R_{16}$ denotes hydrogen or a $C_1$-$C_4$ alkyl group such as methyl and ethyl, $R_{17}$ denotes a $C_1$-$C_4$ alkyl group such as methyl and ethyl or a group corresponding to the formula: —$R_{18}$—$N(R_{16})_2$, with $R_{18}$ representing a —$CH_2$—$CH_2$—, —$CH_2$—$CH_2$—$CH_2$—, or —$CH_2$—$CH(CH_3)$— group and $R_{16}$ having the meanings given above, and also the higher homologues of these groups, containing up to 6 carbon atoms.

8) Amphoteric polymers of the type -D-X-D-X-, chosen from:

a) polymers obtained by the action of chloroacetic acid or sodium chloroacetate on compounds comprising at least one unit of formula:

-D-X-D-X-D-                (X)

where D denotes a group

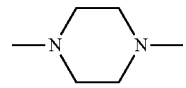

and X denotes the symbol E or E', where E or E', which may be identical or different, denote a divalent group that is an alkylene group with a straight or branched chain containing up to 7 carbon atoms in the main chain, which is unsubstituted or substituted with hydroxyl groups and which can comprise, in addition to oxygen, nitrogen and sulfur atoms, 1 to 3 aromatic and/or heterocyclic rings; the oxygen, nitrogen and sulfur atoms being present in the form of ether, thioether, sulfoxide, sulfone, sulfonium, alkylamine or alkenylamine groups, hydroxyl, benzylamine, amine oxide, quaternary ammonium, amide, imide, alcohol, ester and/or urethane groups.

b) polymers of formula:

-D-X-D-X-                (XI)

where D denotes a group

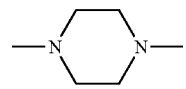

and X denotes the symbol E or E' and at least once E'; E having the meaning given above and E' is a divalent group that is an alkylene group with a straight or branched chain containing up to 7 carbon atoms in the main chain, which is unsubstituted or substituted with one or more hydroxyl groups and which contains one or more nitrogen atoms, the nitrogen atom being substituted with an alkyl chain that is optionally interrupted with an oxygen atom and necessarily comprising one or more carboxyl functions or one or more hydroxyl functions, betainized by reaction with chloroacetic acid or sodium chloroacetate.

9) ($C_1$-$C_5$)alkyl vinyl ether/maleic anhydride copolymers partially modified by semiamidation with an N,N-dialkylaminoalkylamine such as N,N-dimethylaminopropylamine or by semiesterification with an N,N-dialkanolamine. These copolymers may also comprise other vinyl comonomers such as vinylcaprolactam.

According to a preferred embodiment of the invention, the amphoteric fixing polymers that may be used in the aerosol device according to the invention may be chosen from branched block copolymers comprising:

(a) nonionic units derived from at least one monomer chosen from $C_1$-$C_{20}$ alkyl (meth)acrylates, N-mono-($C_2$-$C_{12}$ alkyl)(meth)acrylamides and N,N-di($C_2$-$C_{12}$ alkyl)(meth) acrylamides, (b) anionic units derived from at least one monomer chosen from acrylic acid and methacrylic acid, and (c) polyfunctional units derived from at least one monomer comprising at least two polymerizable unsaturated functional groups, and preferably having a structure consisting of hydrophobic blocks onto which are fixed, via polyfunctional units (c), several blocks that are more hydrophilic.

Preferably, the amphoteric polymers have at least two glass transition temperatures (Tg), at least one of which is greater than 20° C. and the other of which is less than 20° C.

The preferred amphoteric polymers are polymers comprising units deriving:

a) from at least one monomer chosen from acrylamides or methacrylamides which are substituted on the nitrogen by an alkyl group, b) from at least one acidic comonomer containing one or more reactive carboxylic groups, and c) from at least one basic comonomer such as acrylic and methacrylic acid esters containing primary, secondary, tertiary and quaternary amine substituents, and the product of quaternization of dimethylaminoethyl methacrylate with dimethyl or diethyl sulfate.

Mention may be made in particular of the polymers sold under the name Amphomer by the company National Starch.

The nonionic fixing polymers that may be used according to the present invention are chosen, for example, from:

polyalkyloxazolines;

vinyl acetate homopolymers;

vinyl acetate copolymers, for instance copolymers of vinyl acetate and of acrylic ester, copolymers of vinyl acetate and of ethylene, or copolymers of vinyl acetate and of maleic ester, for example of dibutyl maleate, acrylic ester homopolymers and copolymers, for instance copolymers of alkyl acrylates and of alkyl methacrylates, such as the products provided by the company Rohm & Haas under the names Primal® AC-261 K and Eudragit® NE 30 D, by the company BASF under the name 8845, or by the company Hoechst under the name Appretan® N9212, copolymers of acrylonitrile and of a nonionic monomer chosen, for example, from butadiene and alkyl (meth)acrylates, such as the products provided under the name CJ 0601 B by the company Röhm & Haas, styrene homopolymers, styrene copolymers, for instance copolymers of styrene and of alkyl (meth)acrylate, such as the products Mowilith® LDM 6911, Mowilith® DM 611 and Mowilith® LDM 6070 provided by the company Hoechst, the products Rhodopas® SD 215 and Rhodopas® DS 910 provided by the company Rhône-Poulenc, copolymers of styrene, of alkyl methacrylate and of alkyl acrylate, copolymers of styrene and of butadiene, or copolymers of styrene, of butadiene and of vinylpyridine, polyamides, vinyllactam homopolymers such as vinylpyrrolidone homopolymers and the polyvinylcaprolactam sold under the name Luviskol® Plus by the company BASF, vinyllactam copolymers, such as a poly(vinylpyrrolidone/vinyllactam) copolymer sold under the trade name Luvitec® VPC 55K65W by the company BASF, poly(vinylpyrrolidone/vinyl acetate) copolymers, such as those sold under the name PVPVA® S630L by the company ISP, Luviskol® VA 73, VA 64, VA 55, VA 37 and VA 28 by the company BASF and poly(vinylpyrrolidone/vinyl acetate/vinyl propionate) terpolymers, for instance the product sold under the name Luviskol® VAP 343 by the company BASF, and poly(vinyl alcohols).

The alkyl groups of the nonionic polymers mentioned above preferably contain from 1 to 6 carbon atoms.

Among the nonionic fixing polymers, it is preferred to use vinyllactam homopolymers or copolymers.

Preferably, the fixing polymer(s) are chosen from anionic, amphoteric and nonionic fixing polymers. More preferably, the fixing polymer(s) are chosen from anionic and/or nonionic fixing polymers.

The fixing polymer(s) are preferably present in a total amount ranging from 0.1% to 20% by weight, preferably from 0.5% to 10% by weight, better still from 1% to 8%, relative to the total weight of the composition.

The composition may also comprise one or more powders, in particular one or more powders comprising one or more water-insoluble mineral compounds.

The powder may be a styling powder, i.e. it may be a powder which has a capacity for shaping the head of hair or for the durability of this shaping.

The capacity for shaping or shaping durability of the powder may especially be due to its chemical nature and/or its geometrical form and/or its arrangement configuration during deposition onto the keratin fibre. Specifically, the irregularities created at the surface of the hair promote the inter-attachment of the fibres.

The powder may be of any form such as lamellar, spherical or oblong, irrespective of the crystallographic form (for example cubic, hexagonal, orthorhombic, rhombohedric or tetragonal). In a preferred embodiment, the powders are not spherical.

The number-average size of the powder may range from 0.001 to 50 µm, better still from 0.002 to 40 µm and even more preferentially from 0.003 to 35 µm.

This number-average size corresponds to the size measured from the statistical distribution of the particle sizes for half of the total number of the particles. This size is referred to as the D50.

In addition, the number-average size of these particles may be measured in the form of a mean value via an observation method with a light microscope, an electronic microscope, or a particle size analyser using laser scattering.

In the case where the particles are not in spherical form, their number-average size may be determined in the form of the mean of the longest or shortest diameter or of the thickness.

The water-insoluble mineral compound(s) are chosen from metal carbonates, oxides and sulfates and from silicates containing magnesium.

For the purposes of the present invention, the term "water-insoluble" refers to a compound whose solubility at spontaneous pH in water at 25° C. and at atmospheric pressure is less than 0.1%.

Examples that may more particularly be mentioned include the carbonates, oxides and sulfates of alkaline-earth metals such as beryllium, magnesium, calcium, strontium, barium and radium, better still magnesium and calcium; the oxides, sulfates and carbonates of aluminium, gallium and indium; and silicates containing magnesium, in particular those containing an amount of magnesium of greater than 10% by weight (on a dry basis) and expressed as magnesium oxide, such as Li—Mg—Na silicates, for instance Laponite XLG sold by the company Rockwood.

More preferentially, use will be made of calcium carbonate, magnesium carbonate, alumina, barium sulfate and/or magnesium oxide, and better still calcium carbonate such as the calcium carbonate sold under the trade name AH Mikhart 40 by the company Provencale S.A. Preferably, these compounds have a mean particle size of from 20 to 50 μm, as water-insoluble mineral compound(s).

When they are present, the water-insoluble mineral compound(s) are present in an amount ranging from 0.1% to 30% by weight, better still from 0.5% to 15% by weight and even more preferentially from 1% to 10% by weight relative to the total weight of the composition.

The composition may also comprise one or more C2-C4 monoalcohols.

As C2-C4 monoalcohols that may be used in the aerosol device of the invention, mention may be made especially of ethanol or isopropanol, or better still ethanol.

When they are present, the C2-C4 monoalcohol(s) are preferably present in an amount ranging from 1% to 80% by weight, better still from 5% to 70% by weight and even more preferentially from 10% to 65% by weight relative to the total weight of the composition.

The composition according to the invention may contain one or more additional organic solvents such as polyols, for instance glycerol, propylene glycol or polyethylene glycols.

It may also contain water.

When it comprises any, the composition contains between 0.1% and 20% by weight of water, preferably between 0.5% and 15% by weight of water and more preferably between 1% and 10% by weight of water relative to the total weight of the composition.

The container of the device according to the invention also comprises one or more propellants.

Examples of propellants that may be used in the aerosol device of the present invention are liquefied gases such as dimethyl ether, chlorinated and/or fluorinated hydrocarbons such as 1,1-difluoroethane, or volatile hydrocarbons especially such as C3-5 alkanes, for instance propane, isopropane, n-butane, isobutane, pentane, isopentane or compressed gases such as air, nitrogen or carbon dioxide, and mixtures thereof.

Mention may be made preferentially of dimethyl ether and C3-5 alkanes and in particular propane, n-butane and isobutane, and mixtures thereof.

The agent(s) may be present in the composition or, as a variant, in the container containing the composition, but separate from the composition.

The agent(s) are preferably present in the composition.

The propellant(s) are preferably present in an amount ranging from 10% to 90% by weight, better still from 15% to 85% by weight and even more preferentially from 20% to 80% by weight relative to the total weight of the composition.

The compositions defined in the invention may also comprise one or more additives chosen from silicones, fatty esters, fatty alcohols, anionic, cationic, nonionic, amphoteric or zwitterionic polymers other than the fixing polymers, fragrances, dyes, UV-protective screening agents, acids, bases, nacres and glitter flakes.

These additives may be present in the composition according to the invention in an amount ranging from 0 to 20% by weight, relative to the total weight of the composition.

A person skilled in the art will take care to select these optional additives and the amounts thereof so that they do not harm the properties of the compositions of the present invention.

The compositions in accordance with the invention are conditioned in an aerosol device comprising a container, also known as a reservoir.

The container is pressurized and comprises the composition to be dispensed. As already mentioned previously, the container contains both the propellant(s) and the other ingredients of the composition, in a single compartment, or as a variant in two compartments. According to the latter variant, the container may be constituted of an outer aerosol reservoir comprising an inner bag hermetically welded to a valve. The various ingredients of the composition are introduced into the inner bag and a propellant is introduced between the bag and the container at a sufficient pressure to make the composition come out in the form of a spray.

The propellant may be a compressed gas that is preferably used at a pressure of between 1 and 12 bar and better still between 9 and 11 bar.

The container is equipped at its top end with a valve that seals the system. The valves that are suitable for the devices according to the invention are especially valves with an internal restriction orifice of between 0.3 and 3 mm, preferably between 0.5 and 2.5 mm and even more preferentially between 0.6 and 2 mm. As a variant, it is possible for these valves to not comprise an internal restriction orifice. The valves may have a nozzle with at least one orifice, better still two orifices between 0.3 and 1 mm and preferably between 0.4 and 0.8 mm in size. They may also be equipped with an additional gas intake (AGI).

They are in particular valves sold by the companies Precision, Coster, Seaquist and Lindal.

The device, conditioned with such a valve, ensures the sealing of the system, and also the dispensing of the composition from the container.

The aerosol device according to the invention also comprises a dispensing head comprising a body and an end part, especially a diffuser, which may be connected to the body. The end part comprises at least two outlet orifices configured to allow spraying of the composition about a longitudinal axis Y of the end part in at least two different directions, which may especially be diametrically opposite, the dispensing head comprising at least first and second chambers, through which the composition stream successively passes before it exits via the outlet orifices.

The first and second chambers may be concentric.

At least one aperture between the first and second concentric chambers may be angularly offset relative to at least one of the outlet orifices. This angular offset is to be understood as being an offset about the axis of the concentric chambers or about the axis of the device, for example.

Thus, the composition stream leaving the diffuser has in particular undergone at least two changes of direction of the stream in the diffuser, or even at least three changes of direction. The term "change of direction" should be understood as meaning that the composition stream passes from a first direction to a second direction, the two directions forming between themselves an angle preferably greater than 60°, or even greater than 90°, better still greater than 120°, or even greater than 150°. In one illustrative embodiment, the composition stream undergoes at least one change of direction of greater than 120°, or even greater than 150°, better still of the order of 180°.

When assembled, the body and the end piece may define several outlet orifices about a longitudinal axis Y of the end piece, in particular in at least two different directions, which are in particular diametrically opposite. Alternatively, the dispensing orifices may be formed directly in the diffuser. They may be formed in a convex portion of the diffuser, for example a portion with a hemispherical shape.

The use of the term "end piece" does not exclude the possibility that the end piece may comprise an attached element defining the end of the dispensing head.

The concentric chambers may be at least partially annular or, indeed, annular. The dispensing head may in particular comprise a first inner chamber and a second outer chamber. The inner and outer chambers may be separated by a separation skirt. This skirt is able to ensure the leaktightness of the chambers.

This separation skirt may be pierced with at least one aperture, or even at least two apertures, allowing the composition stream to pass through. Thus, the composition stream may be separated into at least two distinct streams. The apertures in the separation skirt may be distributed uniformly on the circumference of the separation skirt. For example, they may be diametrically opposite when there are two of them. There may be between 2 and 10 of them.

The second chamber may be surrounded by a peripheral skirt cooperating with the body in such a way as to ensure the closure of the second chamber.

The outlet orifices may be distributed uniformly on the circumference of the peripheral skirt. For example, they are diametrically opposite when there are two of them. There may be between 2 and 10 of them. They may be diametrically opposite in respective pairs.

The dispensing head may be configured to permit spraying of the composition through outlet orifices in at least one direction transverse to a longitudinal axis Y, in particular in at least two different directions, which are in particular diametrically opposite.

The outlet orifices may be coplanar and arranged in an inclined plane relative to the longitudinal axis X. The dispensing head may in particular comprise at least three coplanar outlet orifices, the directions of spraying being in particular arranged at at least 30°, or even at least 60°, or even at least 90° from each other.

The outlet orifices may be angularly offset relative to the aperture(s) of the separation skirt, each by an angle of between 0 and 180°, preferably between 20 and 90°, preferably between 30 and 80°, for example of the order of 45°.

The longitudinal axis Y of the diffuser may constitute an axis of symmetry of the diffuser.

The diffuser is preferably assembled with the body via the top of said body. The diffuser may define the upper axial end of the dispensing head.

The end part, in particular the diffuser, may comprise an upper face of generally curved shape with outward convexity.

The dispensing head may have a supply channel for the composition coming from the container. To this end, the body comprises a central channel intended to allow the composition stream to pass from the container to the diffuser.

The body may define a cannula through which said channel extends, this cannula having a longitudinal axis inclined relative to the longitudinal axis X of the container.

The central channel of the body may comprise a vertical portion, which extends in the longitudinal axis X of the device above the container, and an oblique portion, which is inclined by an angle γ relative to the vertical portion. The angle γ may be between 0 and 90°, preferably between 5 and 40°, or even between 10 and 30°, for example of the order of 15°. The oblique portion of the central channel can receive the diffuser.

The vertical portion of the central channel is intended to receive the stem of the dispensing valve of the container.

The device may be without a nozzle having swirl ducts, which fact simplifies its production. The dispensing orifices may preferably lead directly to the outside, without an attached nozzle. An attached nozzle is understood as a component having at least one outlet orifice and comprising a plane wall in which the outlet orifice is formed, and also a mounting skirt, which can be mounted on a centre post.

Each jet emerging from the diffuser may be oriented generally along an axis not parallel to a longitudinal axis X of the device, in particular obliquely, for example being inclined relative to the longitudinal axis of the device by an angle greater than 10°, preferably greater than 20°, more preferably greater than 30°.

The flow emerging from each outlet orifice can be oriented perpendicularly relative to the axis Y of the diffuser, the outlet orifices being coplanar, for example, and having axes oriented perpendicularly relative to the axis Y of the diffuser.

Alternatively, the jet emerging from each outlet orifice can form an angle with the normal to this axis Y, in such a way that all the jets produce a resulting spray of substantially conical shape. This angle may be a non-zero angle, between 5 and 180°, preferably between 10 and 90°, or even between 20 and 80°, preferably between 25 and 70°, for example of the order of 35°.

The device may comprise at least three outlet orifices, preferably at least four outlet orifices which are preferably not aligned. The distance between the farthest outlet orifices may be less than 25 mm, preferably less than 20 mm, or even less than 15 mm, for example of the order of 12 mm or 10 mm.

The dispensing of the composition can be triggered by tilting the body relative to the container.

A subject of the invention is also the use of the device as described above for spraying a composition through 360°.

Figure 2:
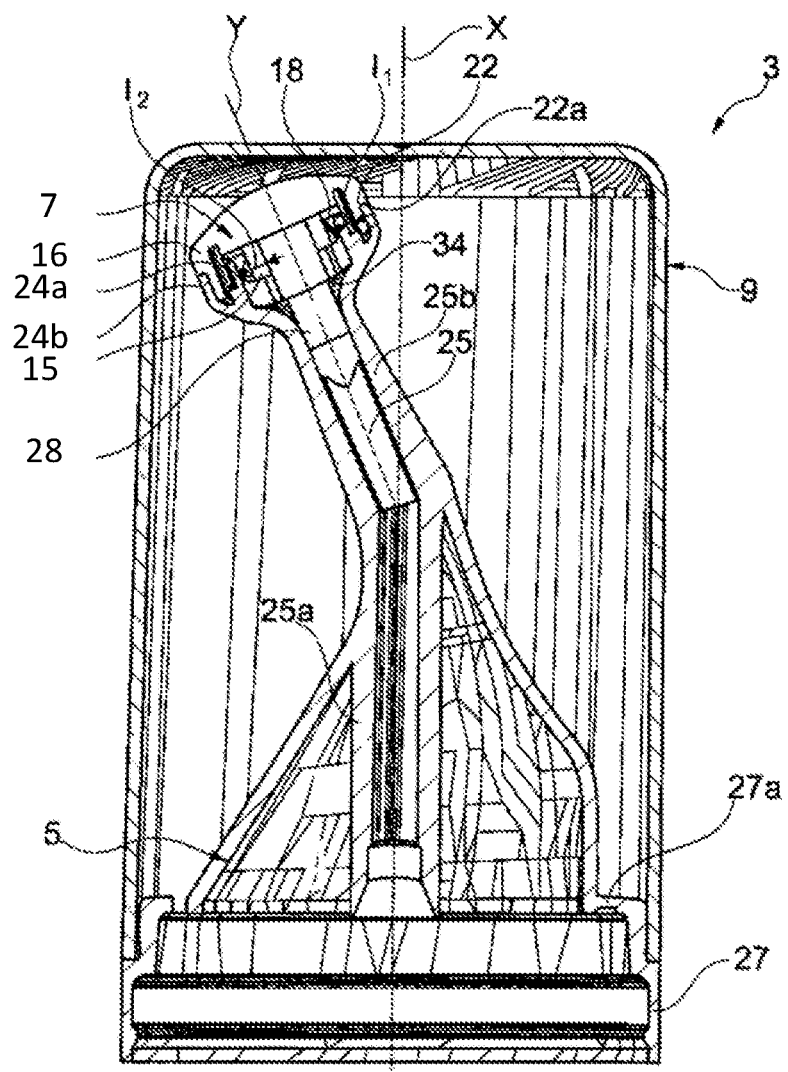
Figure 3:
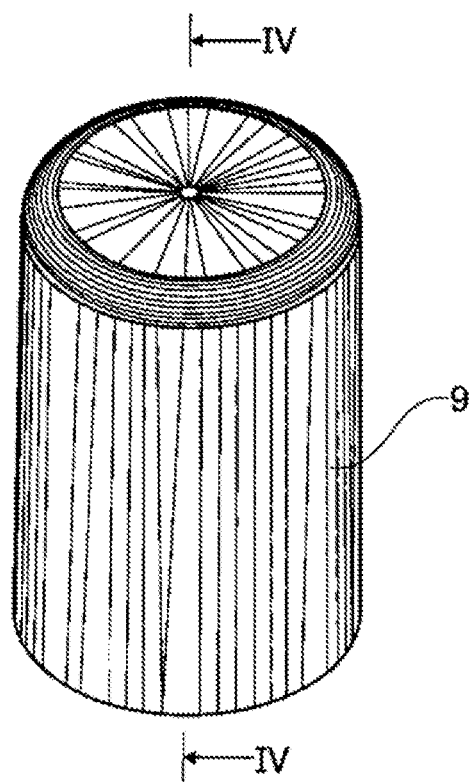
Figure 4:
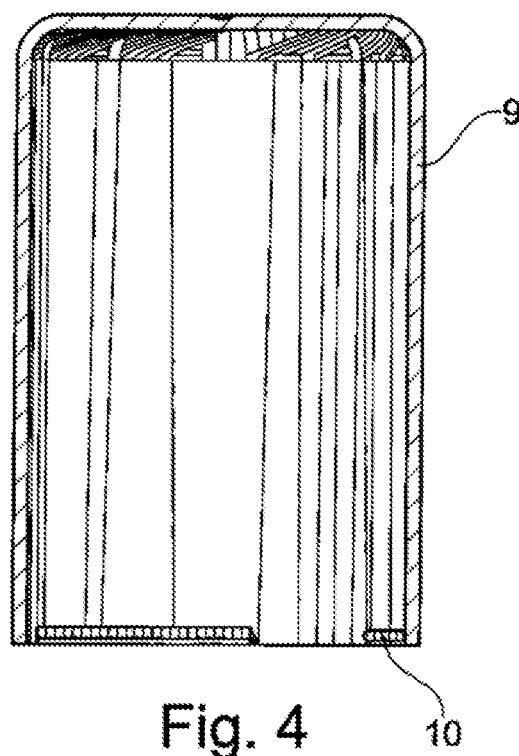
Figure 5:
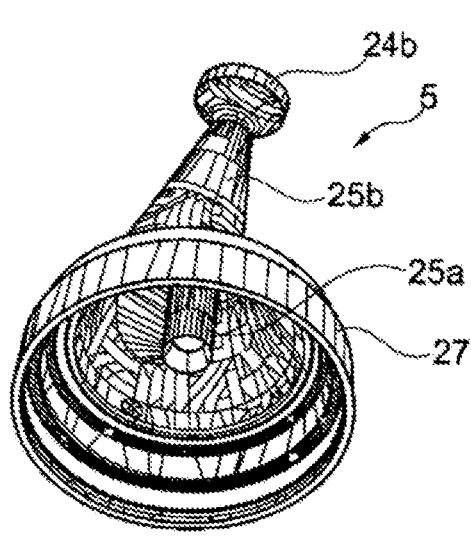
Figure 6:
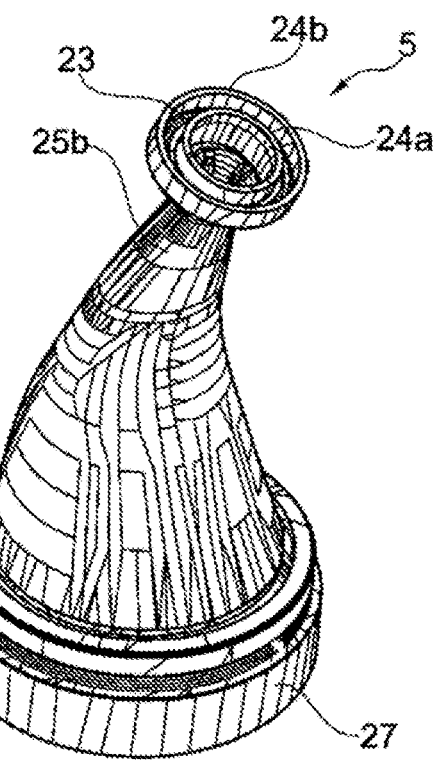
Figure 7:
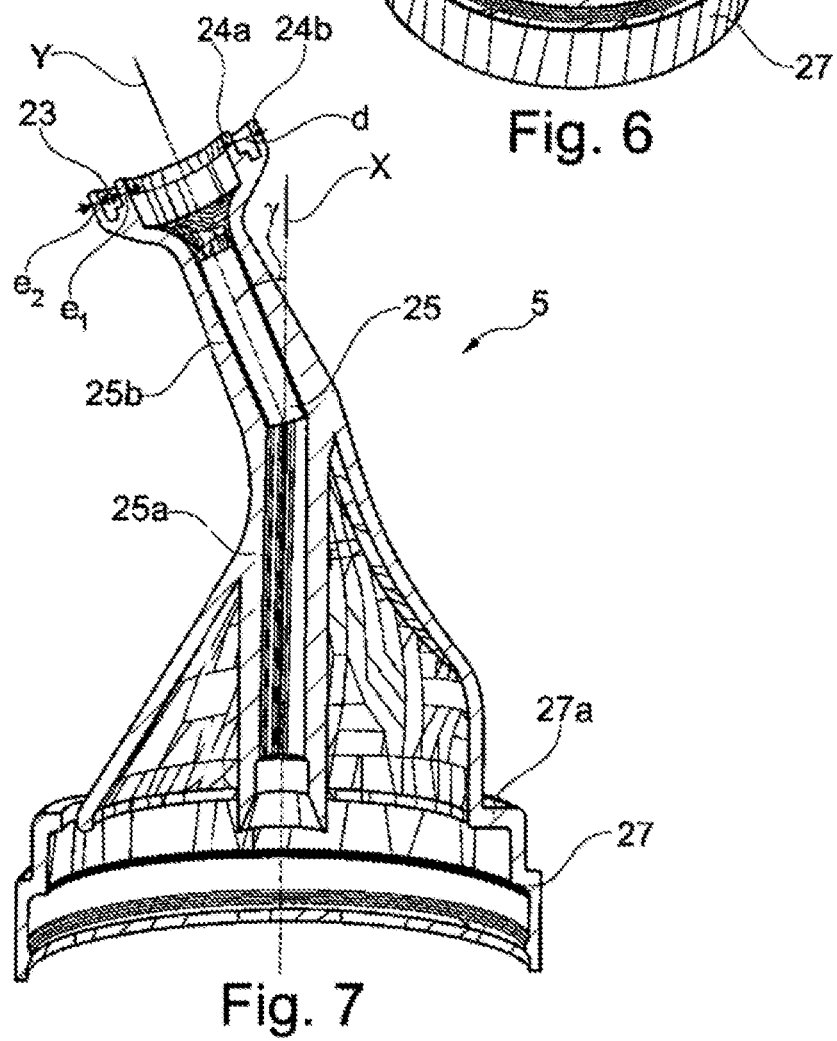
Figure 8:
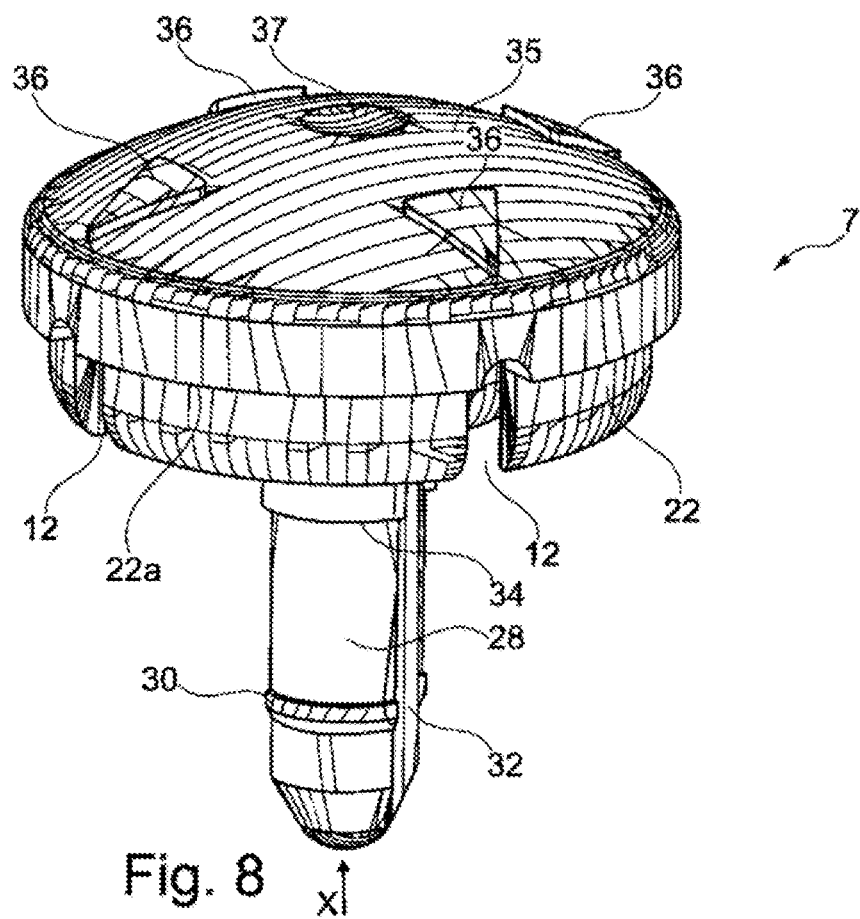
Figure 9:
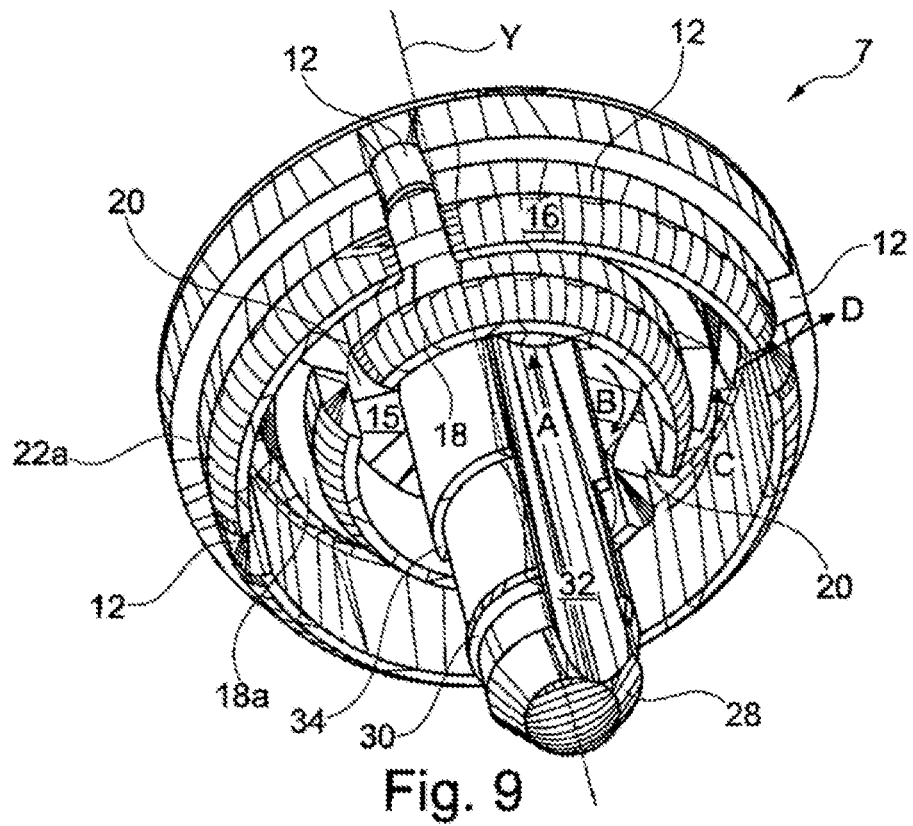
Figure 10:
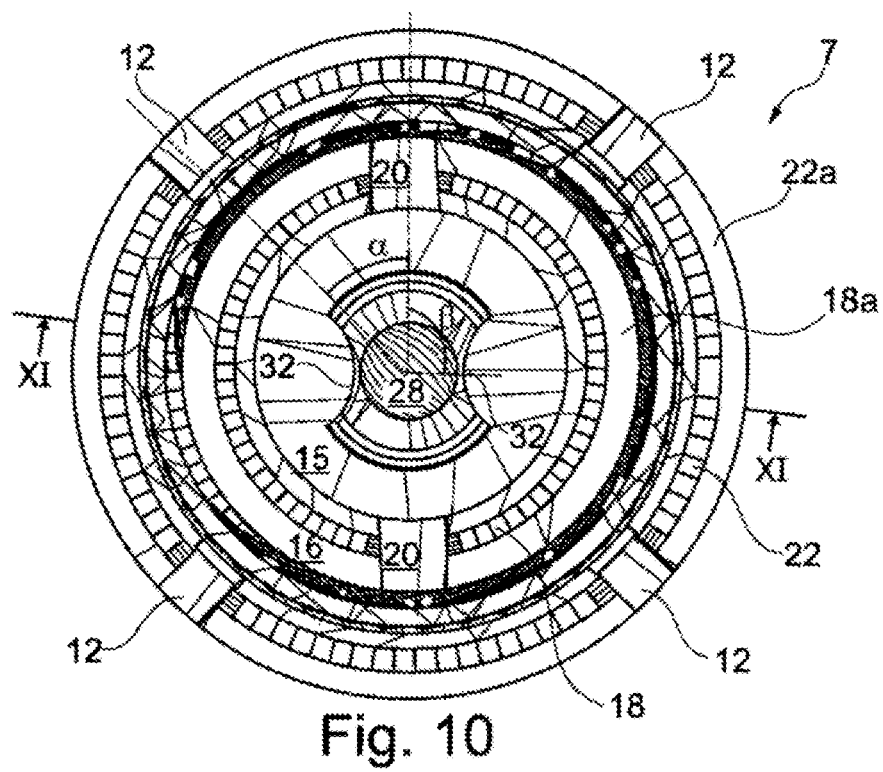
Figure 11:
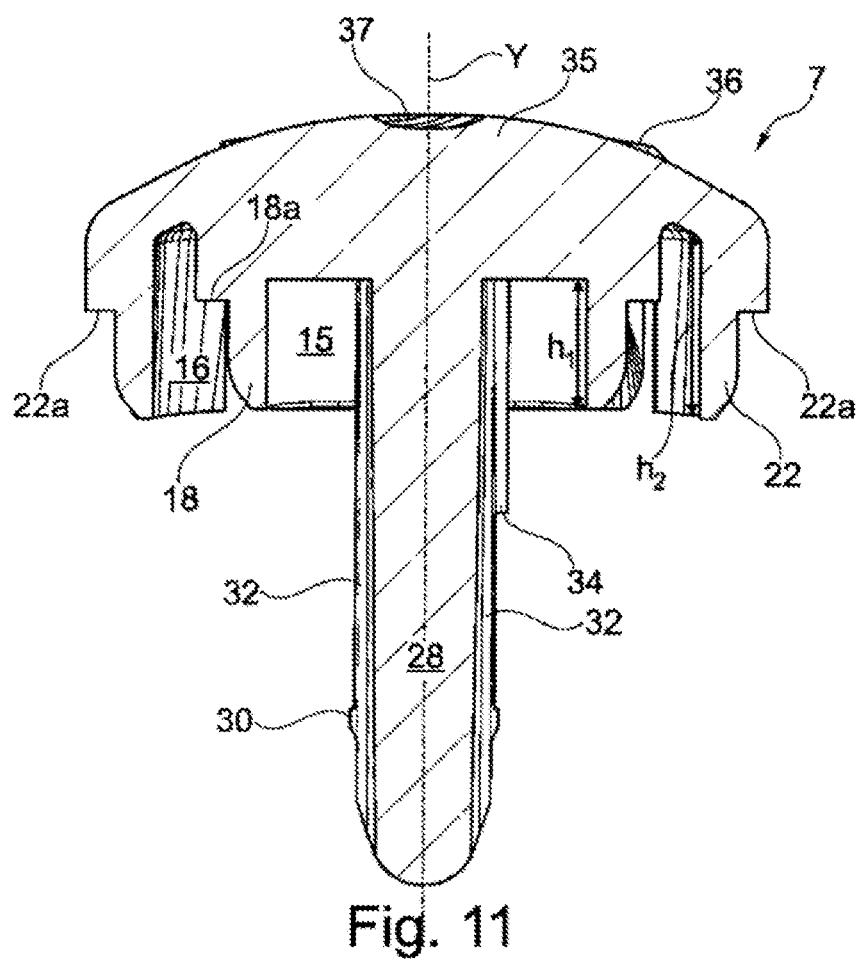
Figure 12:
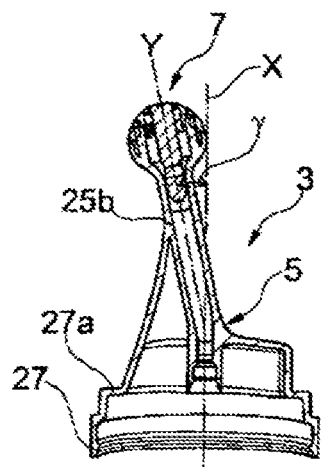
Figure 13:
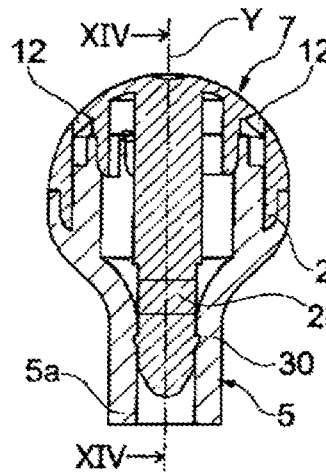
Figure 14:
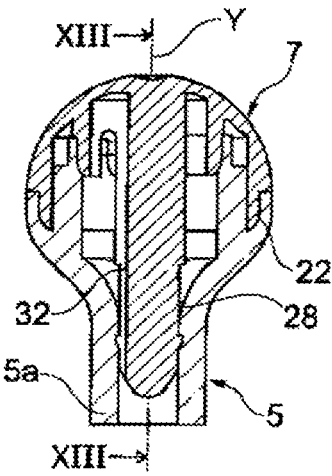
Figure 16:
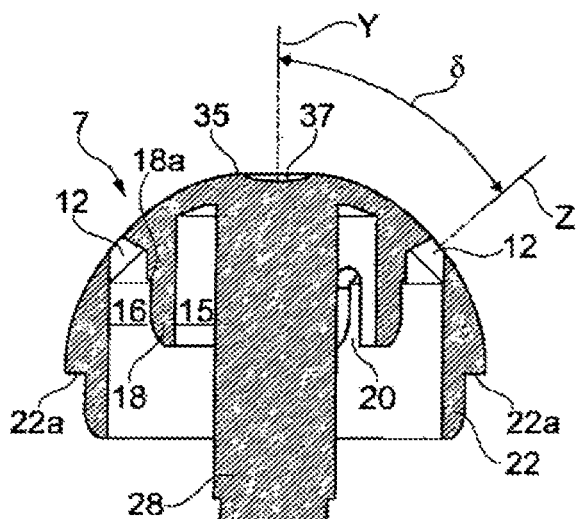
Figure 15:
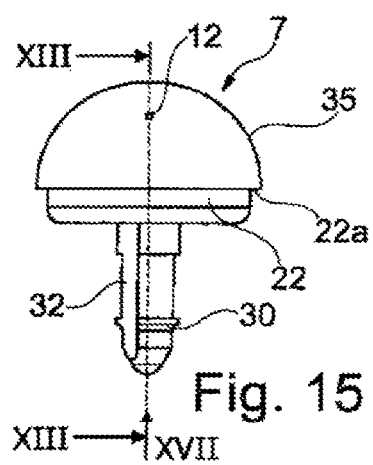
Figure 17:
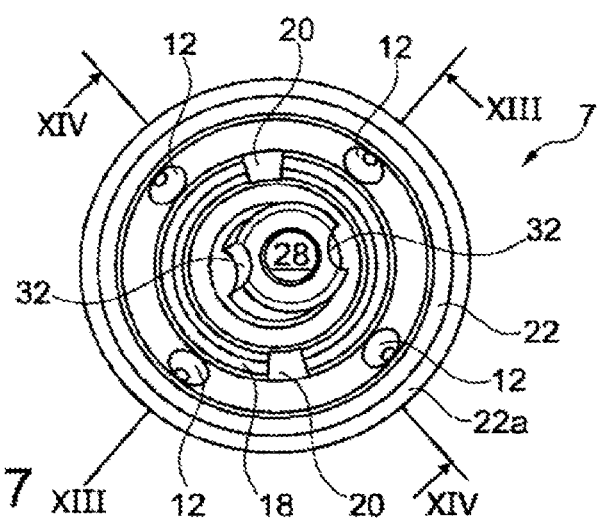
Figure 18:
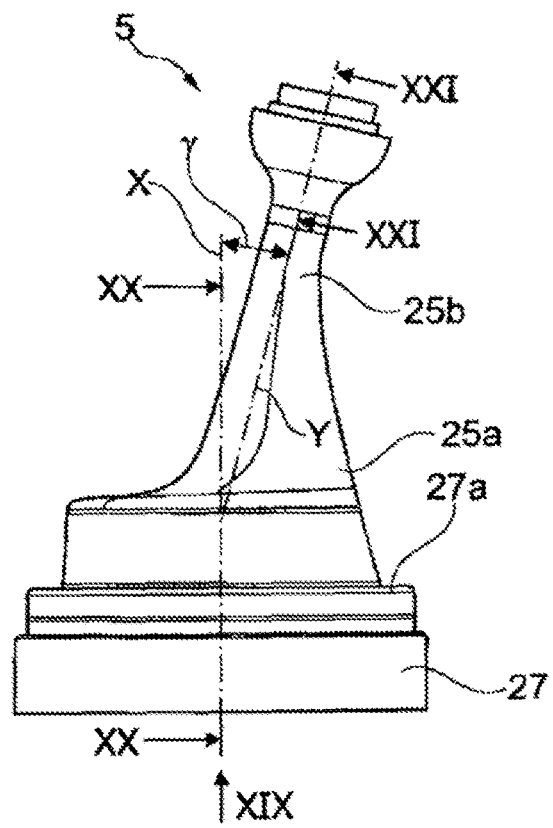
Figure 19:
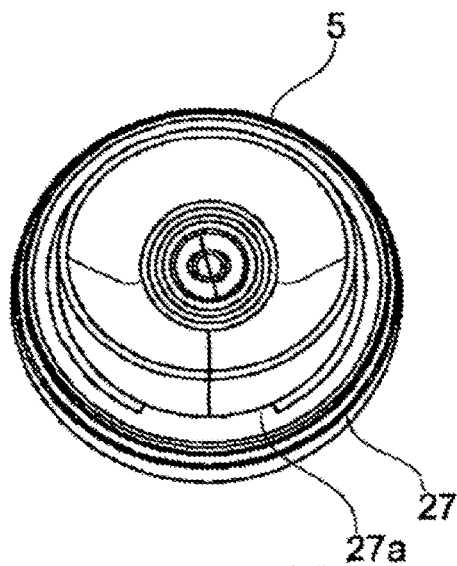
Figure 20:
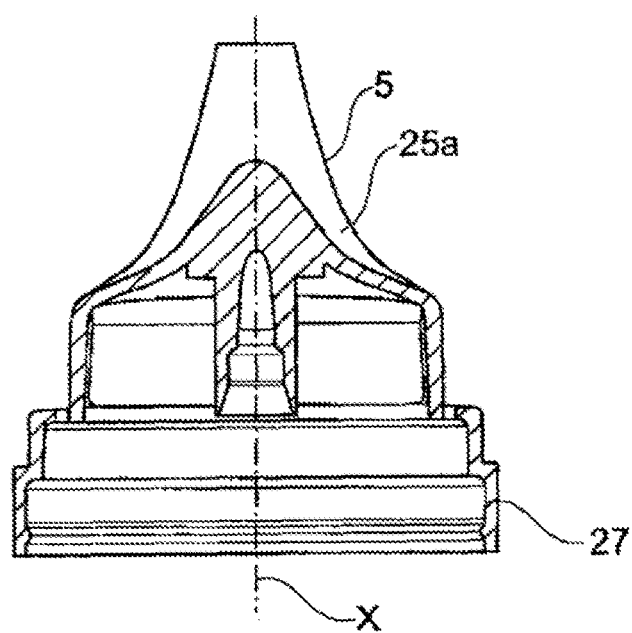
Figure 21:
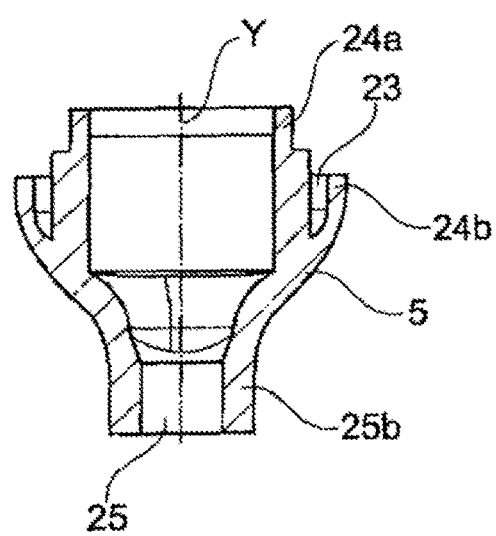

The invention will be better understood on reading the following detailed description of a non-limiting illustrative embodiment thereof and on examining the appended drawing, in which:

FIG. 1 is a side view of a spray device according to the invention,

FIG. 2 is a longitudinal section through the dispensing head of the device in FIG. 1, FIG. 3 is a perspective view of the closure cap of the device in FIGS. 1 and 2, FIG. 4 is a longitudinal section of FIG. 3 along IV-IV, FIGS. 5 and 6 are perspective views of the body of the device in FIGS. 1 and 2, FIG. 7 is a longitudinal section through the body in FIGS. 5 and 6, FIGS. 8 and 9 are schematic and partial perspective views of the diffuser in FIGS. 1 and 2, FIG. 10 is a bottom view along the arrow X in FIGS. 8 and 9, FIG. 11 is a longitudinal section along XI-XI in FIGS. 8 to 10, FIG. 12 is a view, similar to FIG. 7, of an alternative embodiment, FIGS. 13 and 14 are partial longitudinal sections along XIII-XIII and XIV-XIV, respectively, in FIG. 12, FIG. 15 is a perspective view of the diffuser in FIGS. 12 to 14, FIG. 16 is a view, similar to FIG. 13, of the diffuser on its own, FIG. 17 is a view of the diffuser in FIGS. 12 to 16 along the arrow XVII, FIG. 18 is a side view of the body in FIGS. 12 to 17, FIG. 19 is a view thereof along the arrow XIX, FIG. 20 is a cross-sectional view thereof along XX-XX, and FIG. 21 is a cross-sectional view thereof along XXI-XXI.

FIGS. 1 to 11 show a device 1 for spraying a composition, said device 1 comprising a container 2 containing the composition to be sprayed, and a dispensing head 3 which sits on top of the container 2. The initial pressure in the container is, for example, between 1 and 12 bar at 20° C.

The container 2 may comprise a valve holder cup (not shown) crimped onto a body of the container or formed in another way.

The dispensing head 3 comprises a body 5 arranged on the container 2 and cooperating with a diffuser 7. A closure cap 9, visible in FIGS. 3 and 4, is intended to cover the body 5 and the diffuser 7 when the device is not in use. The cap 9 comprises, for example, an annular relief 10 in order to allow it to be held on the container 2 with snap-fit engagement.

The body 5 and the diffuser 7 are configured to allow the composition to be sprayed in at least two different directions, of which there are four in the example described and are distributed uniformly about the axis Y of the diffuser. For this purpose, the diffuser 7 comprises four outlet orifices 12, visible in FIGS. 8 to 10, which will be described in detail below.

During the spraying of the composition, the composition stream coming from the container firstly passes through a central channel 25 of the body 5, which is intended to allow the composition to pass from the container 2 as far as the diffuser 7. This central channel 25 comprises a straight portion 25a, which extends in the longitudinal axis X of the device above the container, and an oblique portion 25b, which extends along the axis Y of the diffuser 7 and which is inclined by an angle γ relative to the straight portion 25a. The angle γ is of the order of 20 to 30°, for example.

The diffuser 7 comprises a central stem 28 allowing it to be fixed to the body 5, in the oblique portion 25b. It is fixed by being inserted by force and with snap-fit engagement. For this purpose, the central stem 28 comprises a fixation relief 30, such as an annular bead, intended to snap-fit behind a corresponding relief of the body 5.

The central stem 28 has a shoulder 34 in order to guarantee leaktightness.

Two longitudinal grooves 32 formed on the central stem 28 allow the composition to pass from the body 5 towards the diffuser 7. They are diametrically opposite each other in the example described. These grooves 32 are oriented along the axis Y of the diffuser. They may have a cross section that is partially circular.

In the diffuser 7, the composition stream passes through a first inner chamber 15 and a second outer chamber 16 concentric to the first.

The diffuser 7 comprises a separation skirt 18 between the first and second chambers 15 and 16. This separation skirt 18 is pierced with two apertures 20 to allow the composition stream to pass through. The latter is thus separated into four distinct streams, of which two opposite streams each emerge from the apertures 20. These apertures are uniformly distributed on the circumference of the separation skirt 18, being diametrically opposite each other. Each aperture 20 preferably extends along the entire height h1 of the separation skirt 18, as is illustrated in FIG. 11. The height h1 of the separation skirt 18 is of the order of 2.5 or 4 mm, for example.

The second chamber 16 is surrounded by a peripheral skirt 22 of the diffuser 7, said peripheral skirt 22 cooperating with the body 5 in such a way as to ensure the closure of the second chamber 16. The peripheral skirt 22 comprises the four abovementioned outlet orifices 12 for ensuring the discharge of the composition to the outside. These outlet orifices 12 are distributed uniformly about the axis Y of the diffuser 7. They may each extend along the entire height h2 of the peripheral skirt or along only part thereof. This height h2 may be of the order of 1.9 or 5 mm.

The chambers 15 and 16 preferably have respective widths I1 and I2 of the order of 1.2 mm.

The outlet orifices 12 may comprise a lower portion, in the form of a slit of constant width formed in the bottom of the skirt 22, and an upper portion, which has a semicircular cross section and is formed in the top of the skirt 22, extending away from the shoulder 22a. The composition emerges from the device via the upper portion of the outlet orifices 12, the lower portion being masked and closed by the body 5.

The outlet orifices may each have a cross section of between 0.05 and 5 $mm^2$, preferably between 0.1 and 2 $mm^2$, for example of the order of 1 $mm^2$.

The outlet orifices may have any suitable geometric shape. In one embodiment, they may have a circular cross section.

The outlet orifices 12 are offset angularly relative to the apertures 20 of the separation skirt 18. For example, they are each offset by an angle α of the order of 45°, as illustrated in FIG. 10.

The apertures 20 are offset relative to the longitudinal grooves 32. For example, they are offset by an angle β of the order of 90°, as illustrated likewise in FIG. 10.

The body 5 comprises an annular groove 23 intended to receive the peripheral skirt 22 of the diffuser 7. This annular groove 23 is delimited by two concentric ribs 24a and 24b which are configured to engage on each side of the peripheral skirt 22. The two ribs 24a and 24b are continuous. They can bear against shoulders 22a and 18a, which are present on the separation skirt 18 and the peripheral skirt 22 respectively, when the body and the diffuser are assembled. They preferably have respective thicknesses e1 and e2 of the order of 0.7 mm. They form between them a distance d of the order of 1.25 mm. The rib 24b closes the lower portion of the outlet orifices 12.

The annular groove 23 and the ribs 24a and 24b are arranged at an end of the body opposite a mounting skirt 27 for mounting the body 5 on the container 2. The rest of the body, in particular the central channel 25 of the body, is connected to the mounting skirt 27 by a hinge 27a. The mounting skirt is preferably fixed with snap-fit engagement on the container, but it may also be fixed to the latter in another way.

The diffuser 7 has an upper face 35 with a generally curved shape, of which the radius of curvature is, for example, of the order of 6 mm.

The upper face 35 of the diffuser 7 has markers in the form of reliefs 36 with the general shape of a triangle, of which the point is oriented towards the edge of the upper face 35 and towards the peripheral skirt 22 in the alignment of the outlet orifices 12. The upper end 35 of the diffuser 7 likewise has a central depression 37, which has a circular contour and accommodates the injection sprue.

The composition stream undergoes at least two changes of direction in the diffuser 7. As illustrated in FIG. 9, the composition stream thus passes from a first direction A in the grooves 32 to a second direction B in the first chamber 15, the two directions A and B forming between them an angle of 90°. The composition stream then passes from the direction B to a direction C in the second chamber 16, with a change of direction of the order of 180°, then adopts a direction D corresponding to the emergence of the composition through an outlet orifice 12.

An alternative embodiment will now be described with reference to FIGS. 12 to 21. In this example, the outlet orifices 12 are formed in the diffuser 7 directly. They are formed in a curved portion of the diffuser 7, of hemispherical shape, having a radius of curvature of the order of approximately 6 mm.

The orifices 12 are each oriented outwards on an axis Z, which forms an angle δ with the axis Y of the diffuser. The angle δ is less than 90°, such that the resulting spray is of conical shape, with the composition being distributed all around the axis Y. The angle δ may be between 10 and 85°, preferably between 20 and 80°, for example between 30 and 75°, or even between 40 and 70°. It may be of the order of 60°, for example.

The dispensing head in FIGS. 12 to 21 also differs from that of FIGS. 1 to 11 in terms of the shape of the body 5. In this illustrative embodiment, the latter comprises a cannula 25b through which said channel 25 extends, this cannula having a longitudinal axis Y inclined relative to the longitudinal axis X of the container.

In addition, the mounting skirt 27 for mounting the body 5 on the container 2 is connected to the rest of the body by a hinge 27a situated, relative to the longitudinal axis X, on the same side as the inclination of the axis Y, in such a way that the longitudinal axis Y of the cannula of a movable part of the body 5 is substantially parallel to the longitudinal axis X of the container during the dispensing of the composition.

The invention is not limited to the examples that have just been described.

For example, the valve of the container may be triggered by being pushed down rather than by tilting.

The number of outlet orifices may be modified, as may their orientation.

The axes of the outlet orifices, along which axes the sprays are emitted, may or may not be coplanar, or they may or may not be contained in the same cone of axis Y.

The example that follows serves to illustrate the invention.

EXAMPLES

In the examples that follow, all the amounts are indicated as weight percentage of product as active materials relative to the total weight of the composition.

The following compositions were prepared from the compounds indicated in the table below.

| COMPOSITIONS | 1 | 2 | 3 | 4 |
|---|---|---|---|---|
| VA/Crotonates/vinyl neodecanoate copolymer[1] | 1.40 | 5.25 | 1.40 | 5.25 |
| Polyvinylpyrrolidone[2] | 0.05 | 0.05 | 0.05 | 0.05 |
| Aminomethylpropanol | 0.15 | 0.55 | 0.15 | 0.15 |
| Fragrance | 0.28 | 0.28 | 0.28 | 0.28 |
| Water | 2.00 | 2.00 | 2.00 | 2.00 |
| Dimethyl ether | 75.00 | 75.00 | 35.00 | 35.00 |
| Ethanol | qs 100 | qs 100 | qs 100 | qs 100 |

[1]Sold under the trade name Resyn 28 - 2930 by Akzo Nobel
[2]Sold under the trade name PVP K90 by ISP.

The compositions are packaged in 150 ml aerosol containers.

The aerosol device D1 according to the invention, shown in FIGS. 12 to 21, was used to package the above compositions. It comprises the following characteristics:

a valve equipped with a nozzle with an orifice 0.42 mm in size and a valve body internal restriction orifice 1.60 mm in size, a dispensing head comprising a cannula which ends with a dome-shaped wall equipped with four outlet orifices of coplanar axes, perpendicular to the longitudinal axis (Y) of the cannula, and uniformly distributed about the axis Y, the four orifices being diametrically opposite in respective pairs. The outlet orifices have a diameter of 0.5 mm. The dispensing head comprises two concentric chambers communicating via two apertures offset by an angle α of the order of 45° relative to the outlet orifices.

A standard aerosol device D2 was used to package the above compositions. It comprises the following characteristics:

a valve equipped with a nozzle with an orifice 0.42 mm in size and an internal restriction orifice 1.6 mm in size, a dispensing head sold under the name V05.701 by the company Coster, equipped with an outlet orifice having swirl ducts (6 ducts), 0.5 mm in diameter.

The compositions were sprayed in pairs onto a malleable head per ½ head, according to the comparisons described below. In all the cases, the same amount of composition was sprayed.

The performance qualities in terms of styling properties, and in particular the ease of shaping and the manageability, were evaluated by an expert, who gave his evaluation per ½ head, attributing a "+" to the side with better performance, a "−" to the side with poorer performance and an "=" in the case of equivalence.

The results are as follows:

|  | Comp. 2 in D1 | Comp. 2 in D2 |
|---|---|---|
| Ease of shaping | + | − |
| Manageability | + | − |

|  | Comp. 4 in D1 | Comp. 4 in D2 |
|---|---|---|
| Ease of shaping | + | − |
| Manageability | + | − |

Thus, it was seen that by using the device D1 according to the invention, greater ease of shaping and greater manageability were afforded than with a standard single-diffusion device, and such was the case irrespective of the content of propellant in the composition.

|  | Comp. 1 in D2 | Comp. 2 in D2 |
|---|---|---|
| Ease of shaping | − | + |
| Manageability | − | + |

|  | Comp. 1 in D1 | Comp. 2 in D2 |
|---|---|---|
| Ease of shaping | + | − |
| Manageability | + | − |

|  | Comp. 3 in D2 | Comp. 4 in D2 |
|---|---|---|
| Ease of shaping | − | + |
| Manageability | − | + |

|  | Comp. 3 in D1 | Comp. 4 in D2 |
|---|---|---|
| Ease of shaping | + | − |
| Manageability | + | − |

Moreover, it was observed that by using a standard single-diffusion diffuser, greater ease of shaping and greater manageability were obtained by using a composition with a higher concentration of fixing polymer than with a composition with a lower concentration of fixing polymer. However, it was also observed that by using the device according to the invention for spraying a composition with a lower concentration of fixing polymer, greater ease of shaping and greater manageability were afforded than with a standard device spraying a composition with a higher concentration of fixing polymer.

The invention claimed is:

1. An aerosol device comprising:
    a container comprising a cosmetic composition comprising a fixing polymer; and
    a dispensing head comprising:
        a body; and
        a diffuser comprising:
            outlet orifices configured to spray the cosmetic composition in different directions with respect to a longitudinal axis of the diffuser;
            first and second concentric chambers through which the composition successively passes before it exits the dispensing head via the outlet orifices;
            a separation skirt that separates the first and second concentric chambers, the separation skirt having at least two apertures configured to allow the cosmetic composition to pass through the separation skirt; and
            at least one aperture disposed between the first and second concentric chambers being angularly offset relative to at least one of the outlet orifices.

2. The aerosol device of claim 1, wherein the fixing polymer is chosen from anionic fixing polymers, amphoteric fixing polymers, nonionic fixing polymers, or any combination thereof.

3. The aerosol device of claim 1, wherein the fixing polymer is chosen from anionic fixing polymers, nonionic fixing polymers, or any combination thereof.

4. The aerosol device of claim 1, wherein the fixing polymer comprises anionic fixing polymers chosen from: copolymers of acrylic and methacrylic acid or salts thereof; crotonic acid copolymers; polyacrylamides bearing carboxylate groups;
    homopolymers or copolymers bearing sulfonic groups; anionic polyurethanes; anionic-grafted silicone polymers; or any combination thereof.

5. The aerosol device of claim 1, wherein the fixing polymer comprises anionic fixing polymers chosen from: polyalkyloxazolines; vinyl acetate homopolymers; vinyl acetate copolymers; homopolymers and copolymers of esters; copolymers of acrylonitrile and a nonionic monomer; styrene homopolymers; styrene copolymers; polyamides; vinyllactam homopolymers; vinyllactam copolymers; polyvinyl alcohols, or any combination thereof.

6. The aerosol device of claim 1, wherein relative to the total weight of the cosmetic composition, the fixing polymers are present in an amount ranging from 0.1% to 20% by weight.

7. The aerosol device of claim 1, wherein the cosmetic composition comprises a water-insoluble powder.

8. The aerosol device of claim 7, wherein the water-insoluble powder comprises a mineral powder chosen from metal carbonates, metal oxides, metal sulfates, magnesium silicates, or any combination thereof.

9. The aerosol device of claim 7, wherein the water-insoluble powder comprises a mineral powder chosen from calcium carbonate, magnesium carbonate, alumina, barium sulfate, magnesium oxide, or any combination thereof.

10. The aerosol device of claim 7, wherein relative to the total weight of the cosmetic composition, the water-insoluble powder is present in an amount ranging from 0.1% to 30% by weight.

11. The aerosol device of claim 1, wherein relative to the total weight of the cosmetic composition, the cosmetic composition comprises a C2-C4 monoalcohol in an amount ranging from 1% to 80% by weight.

12. The aerosol device of claim 1, wherein the cosmetic composition comprises a propellant chosen from air, nitrogen, carbon dioxide, dimethyl ether, n-butane, propane, isobutene, isopentane, 1,1-difluoroethane, or any mixture thereof.

13. The aerosol device of claim 12, wherein relative to the total weight of the composition, the cosmetic composition comprises the propellant in an amount ranging from 15% to 85% by weight.

14. The aerosol device of claim 1, wherein axes of the outlet orifices are coplanar and extend perpendicular to the longitudinal axis of the diffuser.

15. The aerosol device of claim 1, wherein the diffuser comprises a dome-shaped wall comprising the outlet orifices.

16. The aerosol device of claim 1, wherein the body defines a cannula that extends along the longitudinal axis and is inclined relative to a longitudinal axis of the container.

17. A method of shaping hair, the method comprising:
    spraying the hair with an effective amount of a cosmetic composition comprising a fixing polymer, wherein the cosmetic composition is sprayed from a dispensing head comprising:
        a body;
        a diffuser comprising:
            outlet orifices configured to spray the cosmetic composition in different directions with respect to a longitudinal axis of the diffuser;
            first and second concentric chambers through which the composition successively passes before it exits the dispensing head via the outlet orifices;

a separation skirt that separates the first and second concentric chambers, the separation skirt having at least two apertures configured to allow the cosmetic composition to pass through the separation skirt; and at least one aperture disposed between the first and second concentric chambers that is angularly offset relative to at least one of the outlet orifices.

18. The method of claim 17, wherein the method further comprises rinsing the hair after spraying the cosmetic composition on the hair.

19. The method of claim 17, wherein the method further comprises:

wetting the hair before the composition is sprayed onto the hair; and drying the hair after the composition is sprayed onto the hair.

20. An aerosol device comprising:

a container comprising a cosmetic composition comprising a fixing polymer; and a dispensing head comprising:
 a body; and
 a diffuser comprising:
  outlet orifices having coplanar axes that extend in a plane that is perpendicular to a longitudinal axis of the diffuser, such that the outlet orifices are configured to spray the cosmetic composition in different coplanar directions that are perpendicular with respect to the longitudinal axis of the diffuser;

first and second concentric chambers through which the composition successively passes before it exits the dispensing head via the outlet orifices;

a separation skirt that separates the first and second concentric chambers, the separation skirt having at least two apertures configured to allow the cosmetic composition to pass through the separation skirt; and at least one aperture disposed between the first and second concentric chambers being angularly offset relative to at least one of the outlet orifices, wherein the outlet orifices, the first and second concentric chambers, and the separation skirt are symmetrical with respect to the longitudinal axis of the diffuser.

21. The aerosol device of claim 1, wherein the diffuser comprises at least three of the outlet orifices having coplanar axes that extend in the plane perpendicular to the longitudinal axis of the diffuser.

\* \* \* \* \*